US005792746A

United States Patent [19]
Balkovec et al.

[11] Patent Number: 5,792,746
[45] Date of Patent: *Aug. 11, 1998

[54] AZA CYCLOHEXAPEPTIDE COMPOUNDS

[75] Inventors: James M. Balkovec, North Plainfield; Frances Aileen Bouffard, Scotch Plains; Regina M. Black, Cranford, all of N.J.

[73] Assignee: Merck & Co., Inc., Rahway, N.J.

[*] Notice: The term of this patent shall not extend beyond the expiration date of Pat. No. 5,378,804.

[21] Appl. No.: 741,645

[22] Filed: Oct. 28, 1996

Related U.S. Application Data

[63] Continuation of Ser. No. 522,227, filed as PCT/US94/02580, Mar. 10, 1994, published as WO94/21677, Sep. 29, 1994, abandoned.

[51] Int. Cl.$^6$ .............................. A61K 38/12; C07K 7/52
[52] U.S. Cl. ............................ 514/11; 514/9; 514/2; 530/317; 930/270
[58] Field of Search ....................... 530/317; 514/9, 514/11; 930/270

[56] References Cited

U.S. PATENT DOCUMENTS

| | | | |
|---|---|---|---|
| 4,287,120 | 9/1981 | Abbott et al. | 530/317 |
| 4,293,485 | 10/1981 | Debono | 530/317 |
| 4,293,489 | 10/1981 | Debono | 530/317 |
| 4,320,053 | 3/1982 | Abbott et al. | 530/317 |
| 4,931,352 | 6/1990 | Fromtling et al. | 435/71.3 |
| 5,021,341 | 6/1991 | Giacobbe et al. | 435/71.1 |
| 5,159,059 | 10/1992 | Balkovec et al. | 530/317 |
| 5,166,135 | 11/1992 | Schmatz et al. | 514/11 |
| 5,194,377 | 3/1993 | Schwartz et al. | 435/71.1 |
| 5,202,309 | 4/1993 | Schwartz et al. | 514/11 |
| 5,378,804 | 1/1995 | Balcovec et al. | 530/317 |
| 5,514,650 | 5/1996 | Balcovec et al. | 514/11 |
| 5,516,756 | 5/1996 | Balcovec et al. | 514/11 |
| 5,516,757 | 5/1996 | Balcovec et al. | 514/11 |

FOREIGN PATENT DOCUMENTS

| | | |
|---|---|---|
| 851 310 | 8/1977 | Belgium . |
| 859 067 | 3/1978 | Belgium . |
| 0359529 | 3/1990 | European Pat. Off. . |
| 0405997 | 1/1991 | European Pat. Off. . |
| 0 561 639 A1 | 9/1993 | European Pat. Off. . |
| 2340947 | 9/1977 | France . |
| 2365554 | 4/1978 | France . |
| 2 065 130 A | 6/1981 | United Kingdom . |

OTHER PUBLICATIONS

Sepkowitz, et al., . . . "Pneumocystis Carinii Pneumonia . . . " JAMA, 267, No. 6, pp. 832–837, Feb. 12, 1992.

Jacobs, et al., . . . "A Cluster of Pneumocystis Carinii Pneumonia . . . " NEJM, 324, No. 4, pp. 246–250, Jan. 24, 1991.

Walzer, . . . "Pneumocystis Carinii—New Clinical Spectrum . . . " NEJM, 324, No. 4, pp. 263–265, Jan. 24, 1991.

Gautier, et al., . . . "Unexplained CD4-Postive T-cell Deficiency . . . " Clinical and Experimental Allergy, 21, pp. 63–66 (1991).

Poplin et al., . . . "Pneumocystis Carinii Pneumonia in Patients . . . " Cancer, 68, pp. 193–194, Jul. 1, 1991.

Bartlett, et al., . . . "Pneumocystis Carinii, An Opportunist . . . " Clinical Microbiology Reviews, 4, No. 2, pp. 137–149, Apr. 1991.

Henson, et al., . . . "Pneumocystis Carinii Pneumonia in Patients . . . " Arch. Neurol., 48, pp. 406–409, Apr. 1991.

Balkovec et al., Tet. Let. 33 No. 32, 4529–4532 (1992).

Zambias, et al., J. Med. Chem., 35 No. 15, pp. 2843–2855 (1992).

Schwartz, et al., J. Antibiotics, 45 No. 12, pp. 1853–1866 (1992).

Osmond et al., Changes in AIDS Survival Time in Two San Francisco Cohorts of Homosexual Men 1983 to 1993, JAMA, 271, No. 14, Apr. 13, 1994.

*Primary Examiner*—Cecilia J. Tsang
*Assistant Examiner*—Michael Borin
*Attorney, Agent, or Firm*—Elliott Korsen; Mark R. Daniel

[57] ABSTRACT

Ceretain aza cyclohexapeptide compounds have been found to have superior antibiotic properties. Novel processes for their preparation are also described.

4 Claims, No Drawings

AZA CYCLOHEXAPEPTIDE COMPOUNDS

This is a continuation of application Ser. No 08/522,227, filed as PCT/US94/02580, Mar. 10, 1994 published as WO94/21677, Sep. 29, 1994, now abandoned.

The present invention is directed to certain aza cyclohexapeptide compounds and to processes for their preparation.

The aza cyclohexapeptide compounds of the present invention, Compound I (Seq ID Nos. 1–15) are characterized in having a nitrogen attached to the cyclohexapeptide ring at the 5-carbon of the 4-hydroxy ornithine component (hereinafter "C-5-orn") and may be represented by the formula

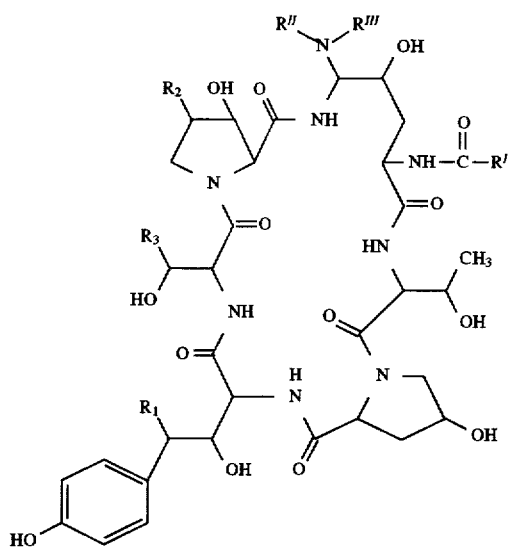

wherein
$R_1$ is H or OH
$R_2$ is H, $CH_3$ or OH
$R_3$ is H, $CH_3$, $CH_2CN$, $CH_2CH_2NH_2$ or $CH_2CONH_2$
$R'$ is $C_9$–$C_{21}$ alkyl, $C_9$–$C_{21}$ alkenyl, $C_1$–$C_{10}$ alkoxyphenyl or $C_1$–$C_{10}$ alkoxynaphthyl
$R''$ is H, $C_1$–$C_4$ alkyl, $C_3$–$C_4$ alkenyl, $(CH_2)_{2-4}OH$, $(CH_2)_{2-4}NR^{IV}R^V$, $CO(CH_2)_{1-4}NH_2$
$R'''$ is H, $C_1$–$C_4$ alkyl, $C_3$–$C_4$ alkenyl, $(CH_2)_{2-4}OH$, $(CH_2)_{2-4}NR^{IV}R^V$, or
$R''$ and
$R'''$ taken together are —$(CH_2)_4$—, —$(CH_2)_5$—, —$(CH_2)_2O(CH_2)_2$— or —$(CH_2)_2$—NH—$(CH_2)_2$—
$R^{IV}$ is H or $C_1$–$C_4$ alkyl
$R^V$ is H or $C_1$–$C_4$ alkyl; and
acid addition salts thereof.

Where the expression "alkyl", "alkenyl" or "alkoxy" is employed, it is intended to include branched as well as straight chain radicals.

The compounds of the present invention are generally obtained as mixtures of stereoisomeric forms in which one form usually predominates. Conditions may be adjusted by means within the normal skill of the skilled artisan to obtain predominantly the desired isomer. The compounds with preferred stereoisomeric form designated herein as the "normal" form may be seen in the working examples with the dashed lines below the plane at the "C-5-orn" position. The designation "epi" has been employed for those compounds in which the group at the "C-5-orn" position is above the plane.

Pharmaceutically acceptable salts suitable as acid addition salts are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in Journal of Pharmaceutical Science, 66, 2 (1977).

Representative nuclei for the aza derivatives of the present invention (Compound I) and the sequence ID for these compounds may be seen in the following table. Since the peptide nuclei would be the same irrespective of substituents $R'$, $R''$ or $R'''$, and since the sequence identification number is assigned for the nuclear variations, the amines and salts have the same sequence ID's.

| Aza Compound | $R_1$ | $R_2$ | $R_3$ | SEQ ID NO |
|---|---|---|---|---|
| I-1 | H | H | $CH_2CONH_2$ | 1 |
| I-2 | H | H | $CH_2CN$ | 2 |
| I-3 | H | H | $CH_2CH_2NH_2$ | 3 |
| I-4 | OH | H | $CH_2CONH_2$ | 4 |
| I-5 | OH | H | $CH_2CN$ | 5 |
| I-6 | OH | H | $CH_2CH_2NH_2$ | 6 |
| I-7 | OH | $CH_3$ | $CH_2CONH_2$ | 7 |
| I-8 | OH | $CH_3$ | $CH_2CN$ | 8 |
| I-9 | OH | $CH_3$ | $CH_2CH_2NH_2$ | 9 |
| I-10 | OH | $CH_3$ | $CH_3$ | 10 |
| I-11 | OH | $CH_3$ | H | 11 |
| I-12 | OH | OH | $CH_2CONH_2$ | 12 |
| I-13 | OH | OH | $CH_2CN$ | 13 |
| I-14 | OH | OH | $CH_2CH_2NH_2$ | 14 |
| I-15 | H | $CH_3$ | $CH_3$ | 15 |

One of the compounds which is particularly outstanding for the control of mycotic infections is a compound identifiable as Compound I-6 wherein $R''$ is H, $R'''$ is $CH_2CH_2NH_2$ and $R'$ is 9,11-dimethyltridecyl (DMTD), and which may be referred to specifically as Compound I-6-1 (Seq ID No. 6).

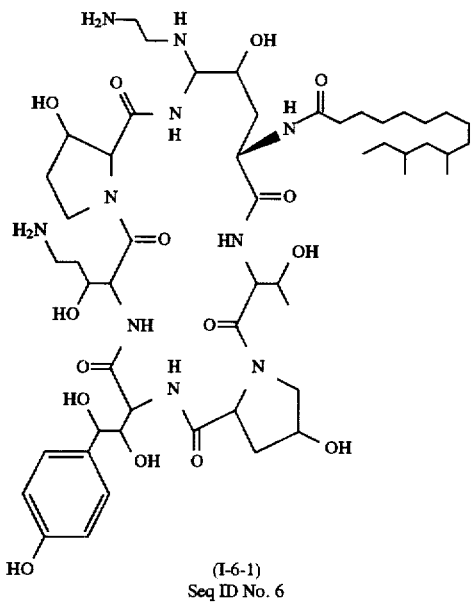

(I-6-1)
Seq ID No. 6

In the above designation I-6-1 refers to the first compound in which the nuclear arrangement is I-6. Since in all the compounds of the present invention the substituent at the "C-5-orn" is nitrogen, the substituents on said nitrogen may vary and still all compounds which have the same $R_1$, $R_2$ and $R_3$ would be Seq ID No. 6.

The compounds are soluble in lower alcohols, and polar aprotic solvents such as dimethylfomiamide (DMF), dimethyl sulfoxide (DMSO) and pyridine. They are insoluble in solvents such as diethyl ether and acetonitrile.

The compounds of the present invention are useful as an antibiotic, especially as an antifungal agent or as an antiprotozoal agent. As antifungal agents they are useful for the control of both filamentous fungi and yeasts. They are especially adaptable to be employed for the treatment of mycotic infections in mammals, especially those caused by Candida species such as *C. albicans, C. tropicalis* and *C. pseudotropicalis*, Cryptococcus species such as *C. neoformans* and Aspergillus species such as *A. fumigatus, A. flavus, A. niger*. They are also useful for the treatment and/or prevention of *Pneumocystis carinii* pneumonia to which immune-compromised patients are especially susceptible as hereinafter described.

The compounds of the present invention may be prepared from cyclopeptides having the formula

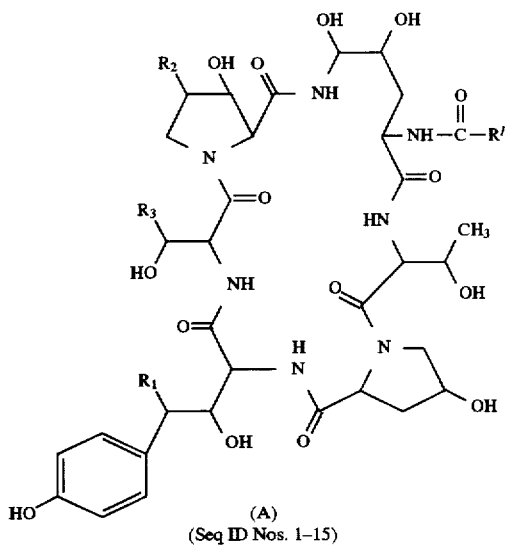

(A)
(Seq ID Nos. 1–15)

by a series of reactions in which the oxygen atom at the "C-5-orn" (which also may be referred to as the hemiaminal position) is ultimately replaced by nitrogen. The starting materials may be natural products or modified natural products as subsequently described. When $R_1$ is hydrogen instead of hydroxyl, the product aza compounds may be prepared by an alternate series of reactions. The method applicable for the preparation of compounds in which $R_1$ may be either H or OH is first described.

The sequence IDs of the starting materials are seen in the following table:

| Compound | $R_1$ | $R_2$ | $R_3$ | Starting Material SEQ ID NO. |
|---|---|---|---|---|
| A-1 | H | H | $CH_2CONH_2$ | 16 |
| A-2 | H | H | $CH_2CN$ | 17 |
| A-3 | H | H | $CH_2CH_2NH_2$ | 18 |
| A-4 | OH | H | $CH_2CONH_2$ | 19 |
| A-5 | OH | H | $CH_2CN$ | 20 |
| A-6 | OH | H | $CH_2CH_2NH_2$ | 21 |
| A-7 | OH | $CH_3$ | $CH_2CONH_2$ | 22 |
| A-8 | OH | $CH_3$ | $CH_2CN$ | 23 |
| A-9 | OH | $CH_3$ | $CH_2CH_2NH_2$ | 24 |
| A-10 | OH | $CH_3$ | $CH_3$ | 25 |
| A-11 | OH | $CH_3$ | H | 26 |
| A-12 | OH | OH | $CH_2CONH_2$ | 27 |
| A-13 | OH | OH | $CH_2CN$ | 28 |
| A-14 | OH | OH | $CH_2CH_2NH_2$ | 29 |
| A-15 | H | $CH_3$ | $CH_3$ | 30 |

Compounds A-4 and A-7 have been identified in the literature (J. Antibiotics 45, 1855–60 December 1992) as pneumocandin $B_o$ and pneumocandin $A_o$ when R'=DMTD.

When in Compound A-1, $R_1$ and $R_2$ are represented by any of the possible variables and $R_3$ is —H, $CH_3$ or —$CH_2CONH_2$ (Seq ID Nos. 16, 19, 22, 25–27 and 30), they may be directly employed in the first method. When $R_3$ is —$CH_2CN$ or —$CH_2CH_2NH_2$, the group —$CH_2CONH_2$ may be first converted to —$CH_2CN$ or —$CH_2CH_2NH_2$ as subsequently disclosed and all the modified compounds (Seq ID Nos. 17–18, 20–21, 23–24, 28–29) used in the first method, or alternatively, a compound in which $R_3$ is $CH_2CONH_2$ may be employed to produce a compound with N at the hemiaminal position, and the —$CH_2CONH_2$ of the resulting product then converted to —$CH_2CN$ or —$CH_2CH_2NH_2$.

First, when $R_1$, $R_2$ and $R_3$ of the starting material are the same as that in the product, the following sequence may be employed.

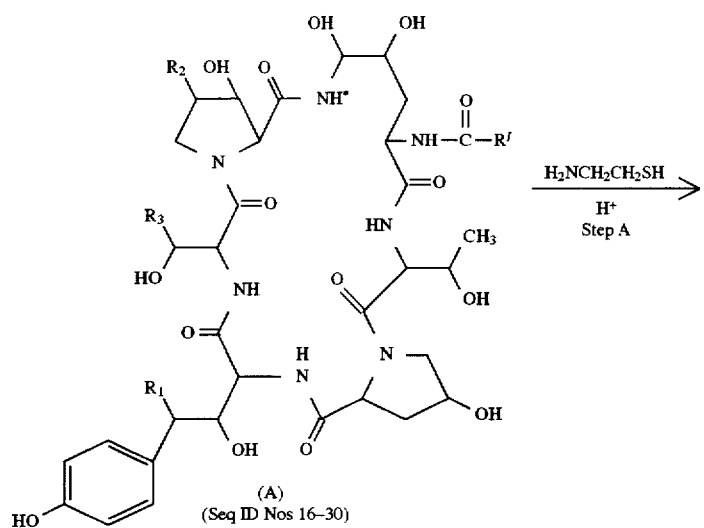
(A)
(Seq ID Nos 16–30)
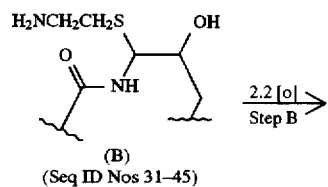
(B)
(Seq ID Nos 31–45)
*The position is the "C-5-orn" or the hemiaminal position.
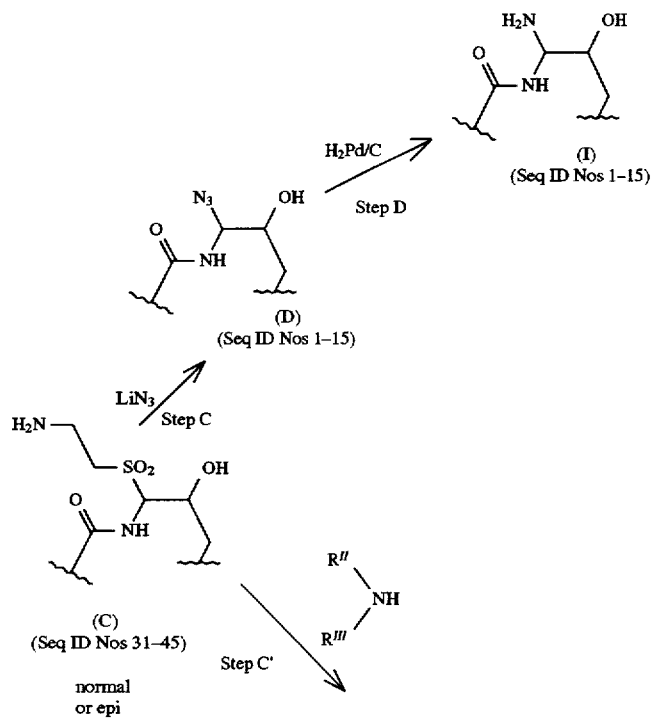

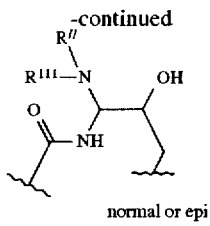

normal or epi (I)
(Seq ID Nos 1–15)

In Step A, the starting material Compound A (Seq ID Nos. 16–30), alkylthiol or arylthiol and acid are caused to react in an aprotic solvent under anhydrous conditions for time sufficient for reaction to take place with the formation of Compound B (Seq ID Nos. 31–45), seen in the following table. Aminoethylthiol has been found to be useful for this step.

| Compound | R₁ | R₂ | R₃ | Sulfur Intermediate SEQ ID |
|---|---|---|---|---|
| B-1 | H | H | CH₂CONH₂ | 31 |
| B-2 | H | H | CH₂CN | 32 |
| B-3 | H | H | CH₂CH₂NH₂ | 33 |
| B-4 | OH | H | CH₂CONH₂ | 34 |
| B-5 | OH | H | CH₂CN | 35 |
| B-6 | OH | H | CH₂CH₂NH₂ | 36 |
| B-7 | OH | CH₃ | CH₂CONH₂ | 37 |
| B-8 | OH | CH₃ | CH₂CN | 38 |
| B-9 | OH | CH₃ | CH₂CH₂NH₂ | 39 |
| B-10 | OH | CH₃ | CH₃ | 40 |
| B-11 | OH | CH₃ | H | 41 |
| B-12 | OH | OH | CH₂CONH₂ | 42 |
| B-13 | OH | OH | CH₂CN | 43 |
| B-14 | OH | OH | CH₂CH₂NH₂ | 44 |
| B-15 | H | CH₃ | CH₃ | 45 |

For Step A, suitable acids include strong organic acid and mineral acids. Examples of strong organic acids are camphorsulfonic acid, p-toluenesulfonic acid and methanesulfonic acid. Mineral acids include hydrochloric acid and hydrobromic acid. Camphorsulfonic acid is preferred.

Suitable solvents include DMF, DMSO, 1-methyl-2-pyrrolidinone and hexamethyl phosphoric triamide (HMPA). DMF or DMSO is preferred.

The reaction is generally carried out at ambient temperature for from 1 to about 10 days.

In carrying out the reaction, the cyclohexapeptide compound, the thiol compound and acid are stirred together in a suitable solvent until the reaction is substantially complete. The reaction mixture then is diluted with water and flash chromatographed on reverse phase resins using 10 to 40 percent acetonitrile/water (containing 0.1% trifluoroacetic acid) as eluant. Trifluoroacetic acid may hereinafter be designated "TFA". The fractions containing the desired product may be concentrated and lyophilized and the lyophilized material purified by preparative high performance liquid chromatography (HPLC).

Appropriate columns for HPLC are commercially available columns sold under trade mark names or trade names such as "ZORBAX" (DuPont), "DeltaPak" (Waters), Bio-Rad (Bio-Rad), "LICHROPREP" RP18 (E. Merck). The specific columns are identified in the working examples.

In Step B, Compound C (Seq ID Nos. 31–45), a sulfone is obtained by the oxidation of Compound B. Suitable oxidizing agents or oxidants include "OXONE," (KHSO₅.KHSO₄.K₂SO₄ 2:1:1, Aldrich Chemicals) metachloroperoxybenzoic acid, and peroxyacetic acid. The sequence ID of Compound C is the same as that of Compound B since the atom attached to the hemiaminal carbon is still sulfur. Thus, the sequence IDs of the sulfones are as follows:

| Compound | R₁ | R₂ | R₃ | Sulfone SEQ ID |
|---|---|---|---|---|
| C-1 | H | H | CH₂CONH₂ | 31 |
| C-2 | H | H | CH₂CN | 32 |
| C-3 | H | H | CH₂CH₂NH₂ | 33 |
| C-4 | OH | H | CH₂CONH₂ | 34 |
| C-5 | OH | H | CH₂CN | 35 |
| C-6 | OH | H | CH₂CH₂NH₂ | 36 |
| C-7 | OH | CH₃ | CH₂CONH₂ | 37 |
| C-8 | OH | CH₃ | CH₂CN | 38 |
| C-9 | OH | CH₃ | CH₂CH₂NH₂ | 39 |
| C-10 | OH | CH₃ | CH₃ | 40 |
| C-11 | OH | CH₃ | H | 41 |
| C-12 | OH | OH | CH₂CONH₂ | 42 |
| C-13 | OH | OH | CH₂CN | 43 |
| C-14 | OH | OH | CH₂CH₂NH₂ | 44 |
| C-15 | H | CH₃ | CH₃ | 45 |

The oxidation of the thioether (Compound B) to the sulfone (Compound C) is carried out with about two molar amounts of the oxidant. When one molar amount of oxidant is employed, the product is a sulfoxide which may then be converted to the sulfone. The sulfoxides may be employed as an intermediate in the formation the aza compounds but the sulfone is preferred. A slight excess over the two molar amount of the oxidizing agent is employed.

The reaction is carried out in an aqueous medium, preferably a mixture of acetonitrile and water. About equal amounts are preferred although a range of 1:9 to 9:1 may be employed.

In carrying out the reaction, the oxidant is added to a solution of Compound B (Seq ID Nos. 31–45) in 1:1 acetonitrile/water and the mixture allowed to stand at ambient temperature for time sufficient to complete the reaction to obtain Compound C generally from about 30 minutes to one hour.

After completion of the reaction, the compound is recovered from the reaction mixture by diluting with water and chromatographing. Reverse phase (C18) flash column chromatography is suitable in this purification step. The preferred eluting agent is 30–45 percent acetonitrile/water (0.1% TFA) in 5 percent step gradients. The appropriate fractions are lyophilized to recover the desired sulfone intermediate, Compound C (Seq ID Nos. 31–45). The intermediate tends to be labile, thus the isolation should be carried out as rapidly as possible.

Compound C may be converted to a compound having a nitrogen directly attached to the "C-5-orn". As seen in the flow diagram, reaction of Compound C with an alkali metal azide produces an azide at that position (Compound D) while reaction with an amine compound (ammonia or amine) produces an amino group at the "C-5-orn" position. (Compound I). Compound D is an important intermediate for most of the compounds of the present invention. Although Compound D has nitrogen at "C-5-orn", since it is not a product. separate sequence ID Nos. are assigned for Compound D. Sequence ID Nos. for Compound D are found in the following table.

| Compound | $R_1$ | $R_2$ | $R_3$ | Azide SEQ ID |
|---|---|---|---|---|
| D-1  | H  | H    | $CH_2CONH_2$   | 46 |
| D-2  | H  | H    | $CH_2CN$       | 47 |
| D-3  | H  | H    | $CH_2CH_2NH_2$ | 48 |
| D-4  | OH | H    | $CH_2CONH_2$   | 49 |
| D-5  | OH | H    | $CH_2CN$       | 50 |
| D-6  | OH | H    | $CH_2CH_2NH_2$ | 51 |
| D-7  | OH | $CH_3$ | $CH_2CONH_2$   | 52 |
| D-8  | OH | $CH_3$ | $CH_2CN$       | 53 |
| D-9  | OH | $CH_3$ | $CH_2CH_2NH_2$ | 54 |
| D-10 | OH | $CH_3$ | $CH_3$         | 55 |
| D-11 | OH | $CH_3$ | H              | 56 |
| D-12 | OH | OH   | $CH_2CONH_2$   | 57 |
| D-13 | OH | OH   | $CH_2CN$       | 58 |
| D-14 | OH | OH   | $CH_2CH_2NH_2$ | 59 |
| D-15 | H  | $CH_3$ | $CH_3$         | 60 |

The azide may be obtained by adding alkali metal azide while stirring at ambient temperature to a solution of the sulfone (Compound C; Seq. ID Nos. 31–45) in an aprotic solvent for time sufficient to complete the reaction with the formation of the azide as determined by HPLC analysis. The reaction mixture then may be diluted with aqueous acid such as trifluoroacetic acid and then chromatographed to separate the desired azide (Compound D) from the reaction mixture. Reverse-phase (C18) flash column chromatography using 10–25 percent acetonitrile/water (0.1% TFA) in 5 percent step gradients is suitable for this procedure.

The azide (Compound D) may then be reduced to a compound having a free amino group which is among the products (Compound I, Seq ID Nos. 1–15) of the present invention.

The reduction may be carried out by mixing the azide compound (Compound I) with Pd/C in a solvent such as glacial acetic acid and hydrogenating under balloon pressure for 10 to 20 hours. The product then may be recovered by first removing the catalyst by filtration and the filtrate lyophilized to obtain the amine compound (Seq ID 1–15) in which the amine is a primary amine.

The amine thus obtained may be converted into a substituted amine as subsequently described.

Compound I in which —$NR''R'''$ is represented by —$NHCH_2CH_2NH_2$ or generically by —$NH(CH_2)_{2-4}NR^{IV}R^V$ may be prepared from the sulfone by a method in which a diamine $H_2N(CH_2)_{2-4}NR^{IV}R^V$ is caused to react with the sulfone (Compound C, Seq ID Nos. 31–45).

The reaction is carried out in an aprotic solvent such as those previously named and at ambient temperature. About tenfold molar excess of the amine compound is employed. The reaction may be carried out over one to several hours.

In carrying out the reaction, the appropriate amine is added to a solution of the sulfone in anhydrous aprotic solvent and the reaction mixture stirred at ambient temperature to obtain Compound I (Seq ID Nos. 1–15) in which the substituent at "C-5-orn" is —$NR''R'''$. The desired compound may then be recovered by diluting with aqueous trifluoroacetic acid and then chromatographing. Reverse phase (C18) flash column chromatography eluting with 10 to 25% acetonitrile/water (0.1% TFA) in 5 percent step gradients is suitable. The appropriate fractions may be lyophilized to recover the product as a trifluoroacetate salt.

The trifluoroacetate salt may be converted by dissolving the salt in water and passing through a Bio-Rad AG2-X8 (Cl–) polyprep column and recovering the product as the hydrochloride salt.

When $R_1$ in formula (I) is hydrogen, Compound I' (Seq ID Nos. 1–3, 15), the nitrogen may be introduced directly into the hemiaminal position by a reaction to form the azide, which then is reduced to an amine which optionally may be alkylated or acylated to obtain the ultimate product. The reaction is seen by the following flow diagram.

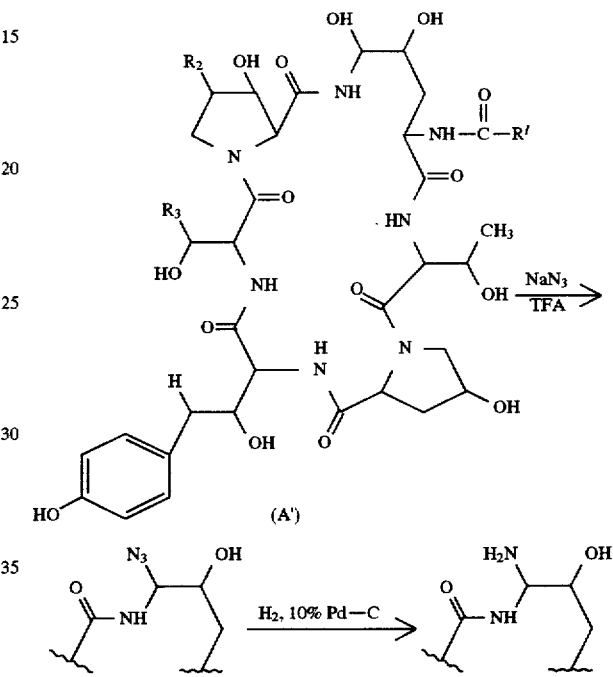

Although $R_1$ is hydrogen in some natural product cyclohexapeptides. $R_1$ is more commonly hydroxyl. Thus, for a number of the compounds, Compound A' in the flow diagram is prepared as a first step from the corresponding compound in which $R_1$ is OH.

The preparation of the reduced compound may be carried out by stirring the appropriate hydroxy compound in $LiClO_4$-diethyl ether at room temperature, adding trifluoroacetic acid, followed by triethylsilane and subjecting the mixture to rapid stirring for from 4 to 10 hours or until the starting hydroxy compound is no longer detectable by analytical HPLC. The reaction mixture is then poured into distilled water to obtain the reduced product as precipitate which then is recovered by conventional procedures. The reduced product thus obtained may be used with or without purification in the preparation of the azide.

Products in which $R_1$ is H, may be obtained by adding the modified cyclohexapeptide to a preformed solution of $HN_3$. $HN_3$ may be prepared from sodium azide and trifluoroacetic acid. The reaction is allowed to take place at room temperature to obtain the azide product which may be recovered by conventional procedures and purified by HPLC.

The purified azide compound may be reduced to the amine compound by hydrogenating with palladium/carbon in a manner similar to that previously described.

The amines, prepared as above and having a primary amino group —$NH_2$ described, may then be alkylated by conventional means to obtain a substituted amino group. Briefly, alkylation may be carried out by causing an appropriately substituted alkyl halide to react with the amine (Compound I, $NR''R'''$=$NH_2$; Sequence ID Nos 1–15) in an aprotic solvent in the presence of a base to obtain the monosubstituted amine (Compound I, $NR''R'''$=$NHR''$ wherein $R''$ is $C_1$-$C_4$ alkyl, $C_3$-$C_4$ alkenyl, $(CH_2)_{2-4}OH$, and $(CH_2)_{2-4}NR^{IV}R^V$). The latter may be recovered from the reaction mixture by conventional procedures.

The amines, prepared as above described and having a primary amino group —$NH_2$, may be acylated by conventional means to obtain an acylated amino group. The acyl group contemplated is $CO(CH_2)_{1-4}NH_2$. Since this is a primary amino group, the amino of the acylating acid is protected such as with a benzyloxycarbonyl group before the acylation is carried out. An activated ester such as the pentafluorophenyl ester is preferably used. The acylation may be carried out in an aprotic solvent in the presence of base such as diisopropylethylamine at ambient temperature for from one to several hours to obtain the acylation product. The product may be recovered by diluting the reaction mixture with methanol and purifying by HPLC. The protecting group may be removed by conventional hydrogenolysis. (Compound I, —$NR''R'''$=—$NHCO(CH_2)_{1-4}NH_2$).

The amine compounds in which the amino group at the hemiaminal position is totally substituted, i.e. when neither $R''$ nor $R'''$ is

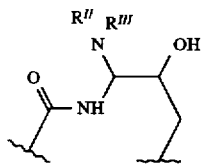

hydrogen, are preferably prepared by reacting the sulfone (Compound B Seq ID No. 31–45) with an appropriately substituted amine $R''R'''NH$. The reaction may be carried out by adding the amine to a stirred solution of the sulfone for time sufficient for reaction to take place. The product may be recovered by purifying by preparative HPLC and lyophilizing the appropriate components.

The invention also embraces acid addition salts. The compound in the normal course of isolation is obtained as an acid addition salt. Generally, it is as a trifluoroacetic acid salt. The salt thus obtained may be dissolved in water and passed through an anion exchange column bearing the desired anion. The eluate containing the desired salt may be concentrated to recover the salt as a solid product.

The compounds of the present invention are active against many fungi and particularly against Candida species. The antifungal properties may be illustrated with the minimum fungicidal concentration (MFC) determination against certain Candida organisms in a microbroth dilution assay carried out in a Yeast Nitrogen Base (DIFCO) medium with 1% dextrose (YNBD).

In a representative assay, compounds were solubilized in 100% dimethyl sulfoxide (DMSO) at an initial concentration of 5 mg/ml. Once dissolved, the drug stock was brought to a concentration of 512 µg/ml by dilution in water such that the final DMSO concentration was about 10 percent. The solution was then dispensed via a multichannel pipetter into the first column of a 96-well plate (each well containing 0.075 ml of YNBD), resulting in a drug concentration of 256 µg/ml. Compounds in the first column were diluted 2-fold across the rows yielding final drug concentration ranging from 256 µg/ml to 0.12 µg/ml.

Four-hour broth cultures of organisms to be tested were adjusted using a spectrophotometer at 600 nm to equal a 0.5 McFarland Standard. This suspension was diluted 1:100 in YNBD to yield a cell concentration of $1-5 \times 10^4$ colony forming units (CFU)/ml. Aliquots of the suspension (0.075 ml) were inoculated into each well of the microtiter plate resulting in a final cell inoculum of $5-25 \times 10^3$ CFU/ml and final drug concentrations ranging from 128 µg/ml to 0.06 µg/ml. Each assay includes one row for drug-free control wells and one row for cell-free control wells.

After 24 hours of incubation, the microtiter plates were shaken gently on a shaker to resuspend the cells. The MIC-2000 inoculator was used to transfer a 1.5 microliter sample from each well of the 96-well microtiter plate to a single reservoir inoculum plate containing Sabouraud dextrose agar (SDA). The inoculated SDA plates were incubated for 24 hours at 35° C. The results were as follows:

| | | | | ORGANISM | | | | |
|---|---|---|---|---|---|---|---|---|
| COMPOUND† | | | | C. albicans | | | C. parapsilosis | C. tropicalis |
| $R_1$ | $R_2$ | $R_3$ | $R''$, $R'''$ | MY 1055 | MY 1028 | MY 1750 | MY 1010 | MY 1012 |
| 1) H | H | —$CH_2CH_2NH_2$ | H; $CH_2CH_2NH_2$ | 0.250 | 0.125 | 0.125 | 0.125 | 0.125 |
| 2) H | H | —$CH_2CONH_2$ | H; $CH_2CH_2NH_2$ | 1.000 | 0.500 | 1.000 | 1.000 | 0.500 |
| 3) H | H | —$CH_2CH_2NH_2$ | H; H | 0.125 | <0.060 | 0.125 | <0.060 | 0.060 |
| 4) OH | H | —$CH_2CH_2NH_2$ | H; $CH_2CH_2NH_2$ | <0.060 | 0.125 | <0.060 | <0.060 | <0.060 |

* $R^I$ = DMTD;
† as acid addition salts

The compounds also show in vivo effectiveness against fungi which may be demonstrated with the same compounds of the in vitro assay.

Growth from an overnight SDA culture of Candida albicans MY 1055 was suspended in sterile saline and the cell concentration determined by hemacytometer count and the cell suspension adjusted to $3.75 \times 10^5$ cells/ml. Then 0.2 milliliter of this suspension was administered I.V. in the tail vein of mice so that the final inoculum was $7.5 \times 10^4$ cells/mouse.

The assay then was carried out by administering aqueous solutions of Compound I at various concentrations intraperitoneally (I.P.), twice daily (b.i.d.) for four consecutive days to 18 to 20 gram female DBA/2 mice, which previously had been infected with Candida albicans in the manner described above. Distilled water was administered I.P. to C.

albicans challenged mice as controls. After seven days, the mice were sacrificed by carbon dioxide gas, paired kidneys were removed aseptically and placed in sterile polyethylene bags containing 5 milliliters of sterile saline. The kidneys were homogenized in the bags, serially diluted in sterile saline and aliquots spread on the surface of SDA plates. The plates were incubated at 35° C. for 48 hours and yeast colonies were enumerated for determination of colony forming units (CFU) per gram of kidneys. Compounds (1), (2), (3) and (4) gave >99 percent reduction of recoverable Candida CFUs at 0.09 and 0.375 mg/kg I.P. twice daily for four consecutive days.

The compounds of the present invention are also useful for inhibiting or alleviating *Pneumocystis carini* infections in immune-comprised patients. The efficacy of the compounds of the present invention for therapeutic or anti-infection purposes may be demonstrated in studies on immunosuppressed rats.

In a representative study, the effectiveness of Compound I-6-1 ($R_1$=OH; $R_2$=H; $R_3$=$CH_2CH_2NH_2$; $R'$=DMTD; $R''$=H; $R'''$=$CH_2CH_2NH_2$) was determined. Sprague-Dawley rats (weighing approximately 250 grams) were immunosuppressed with dexasone in the drinking water (2.0 mg/L) and maintained on a low protein diet for seven weeks to induce the development of pneumocystis pneumonia from a latent infection. Before drug treatment, two rats were sacrificed to confirm the presence of *Pneumocystis carinii* pneumonia (PCP); both rats were found to have infections. Five rats (weighing approximately 150 grams) were injected twice daily for four days subcutaneously (sc) with Compound I-6-1 in 0.25 ml of vehicle (distilled water). A vehicle control was also carried out. All animals continued to receive dexasone in the drinking water and low protein diet during the treatment period. At the completion of the treatment, all animals were sacrificed, the lungs were removed and processed, and the extent of disease determined by microscopic analysis of stained slides. The results of this study showed Compound I-6-1 reduced *P. carinii* cysts in 5 rats by at least 90 percent when dosed at 0.075 mg/g with all rats surviving.

The outstanding properties are most effectively utilized when the compound is formulated into novel pharmaceutical compositions with a pharmaceutically acceptable carrier according to the conventional pharmaceutical compounding techniques.

The novel compositions contain at least a therapeutic antifungal or antipneumocystis amount of the active compound. Generally, the composition contains at least 1% by weight of Compound I. Concentrate compositions suitable for dilutions prior to use may contain 90% or more by weight. The compositions include compositions suitable for oral, topical, parenteral (including intraperitoneal, subcutaneous, intramuscular, and intravenous), nasal, and suppository administration, or insufation. The compositions may be prepacked by intimately mixing Compound I with the components suitable for the medium desired.

Compositions formulated for oral administration may be a liquid composition or a solid composition. For liquid preparation, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with lubricant such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention.

Compositions may be formulated for injection and may take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound may also be solubilized in alcohol/ propylene glycol or polyethylene glycol for drip intravenous administration. These compositions also may be presented in unit dosage form in ampoules or in multidose containers, preferable with added preservative. Alternatively, the active ingredients may be in powder form for reconstituting with a suitable vehicle prior to administration.

The term "unit dosage form" as used in the specification and claims refers to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is for antifungal use any method of administration may be employed. For treating mycotic infections, oral or intravenous administration is usually employed.

When the compound is to be employed for control of pneumocystis infections it is desirable to directly treat lung and bronchi. For this reason inhalation methods are preferred. For administration by inhalation, the compounds of the present inventions are conveniently delivered in the form of an aerosol spray presentation from pressurized packs or nebulisers. The preferred delivery system for inhalation is a metered dose inhalation (MDI) aerosol, which may be formulated as a suspension or solution of Compound I in suitable propellants, such as fluorocarbons or hydrocarbons.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting.

Examples 1–3 illustrate the preparation of the products by the first method described, namely proceeding through the sulfone. This method may be employed in the preparation of any of the compounds but must be employed to obtain a useful yield of product when $R_1$ is OH.

Examples 4 and following illustrate preparation of the products by direct substitution of nitrogen for oxygen into the hemiaminal position "5-orn". This method is preferred when $R_1$ is H, and $R''$ and $R'''$ are H.

Example 3 illustrates employing as starting material, a compound in which $R_3$ has already been reduced to $CH_2CH_2NH_2$ from the natural product state where $R_3$ is $CH_2CONH_2$. Similarly for compounds in which $R_3$ is —$CH_2CN$, the already partially modified compound may be employed.

Examples 9 and 10 illustrate carrying out the conversion of the hemiaminal oxygen to nitrogen and then converting the CH₂CN or CH₂CH₂NH₂.

EXAMPLE 1

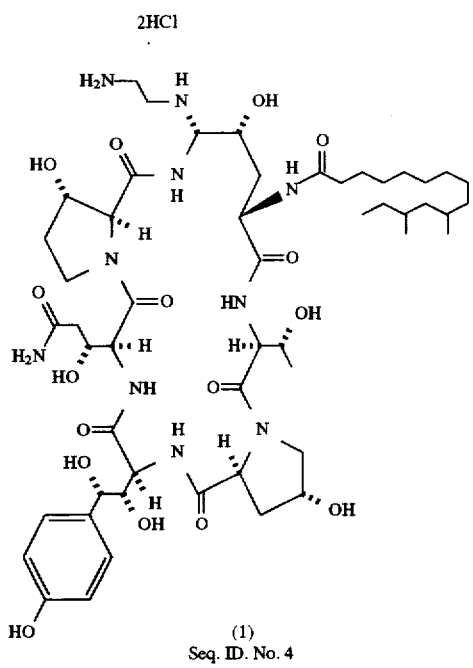

(1)
Seq. ID. No. 4

Part A. Preparation of Intermediate 1-[4-hydroxy-5-(epi)-aminoethylthio-$N^2$-(10,12-dimethyl-1-oxotetradecyl) ornithine]-5-(3-hydroxyglutamine)-6-(3-hydroxyproline) echinocandin B (Seq ID No 34)

A solution of 500 mg (0.47 mmol) of pneurocandin B₀ (Seq ID No 19), 5.34 g (47 mmol) of 2-amino-ethanethiol hydrochloride and 109 mg (0.47 mmol) of (1S)-(+)-10-camphorsulfonic acid in 40 ml anhydrous DMF was stirred at 25° C. for 6 days. The reaction mixture was diluted with 40 ml of water and flash chromatographed on "LICHRO-PREP" RP18 (40–63 μm, 15.0 g) packed with 10% acetonitrile/water. The column was eluted with 10 to 40% acetronitrile/water, collecting two 120 ml fractions at each 10 percent gradient. From the two 40% acetonitrile/water fractions was obtained 185 mg of material which was purified by preparative HPLC "ZORBAX" C8 (21.2×250 mm), eluting with 40–45% acetonitrile/water (0.1% TFA) to obtain 128 mg of 1-[4-hydroxy-5-(epi)-aminoethylthio-$N^2$-(10,12-dimethyl-1-oxotetradecyl)-ornithine]-5-(3-hydroxyglutamine)-6-(3-hydroxyproline)-echinocandin B trifluoroacetate as a white amorphous solid.

¹H NMR (400 MHz, CD₃OD) δ1.34 (d, J=6.3 Hz, 3H), 2.89 (m, 2H), 4.72 (d, J=4.9 Hz, 1H)

FAB-MS (Li), m/e 1131 (MH+Li)⁺

Part B. Preparation of Intermediate Sulfone (Seq. ID 34)

To a stirred solution of the thio compound (444 mg, 0.358 mmol) obtained in Part A, in 15 mL of 1:1 acetonitrile/water was added "OXONE" (324 mg equivalent to 1.06 mmol of potassium hydrogen persulfate). After about 45 minutes, the solution was diluted with an equal volume of water and rapidly chromatographed using reverse-phase (C18) flash chromatography column eluting with 35–43% acetonitrile/water (0.1% TFA) in 2% step gradients. The product containing fractions were lyophilized to obtain 357 mg (86% yield) of the epi-sulfone.

¹H NMR (400 MHz, CD₃OD) δ3.48 (m, 2H), 3.55 (m, 1H), 3.71 (m, 1H), 3.91 (dd, 1H), 4.00 (m, 1H), 5.17 (dd, 1H), 6.76 (d, 2H), 7.16 (d, 2H)

Part C. Preparation of Product of Formula (1); Compound I-4 (Seq ID No 4)

To a stirred solution of 1.2 g (0.945 mmol) of epi-sulfone (prepared as described in Part B) in 20 mL of anhydrous DMF was added ethylenediamine (568 mg, 9.45 mmol). After 1 hour, HPLC analysis (RP-C18, 40% CH₃CN/H₂O (0.1% TFA)) of the reaction mixture indicated complete conversion to two polar products in a ratio of 37:63. Reverse phase (C18) flash column chromatography eluting with 10–40% acetonitrile/water (0.1% TFA) in 5 percent step gradients was followed by lyophilization of the appropriate fractions to provide 200 mg (21% yield) of the normal product as the (bis)-trifluoroacetate salt.

¹H NMR (400 MHz, CD₃OD) δ1.14 (d, J=6.2 Hz, 3H), 2.72 (dd, J=15.4 and 3.8 Hz, 1H), 4.10 (m, H), 5.04 (dd, J=8.7 and 3.2 Hz, 1H), 5.09 (dd, J=8.5 and 4.2 Hz, 1H), 5.18 (br s, 1H), 6.74 (d, J=8.6 Hz, 2H), 7.12 (d, J=8.6 Hz, 2H), 7.47 (d, J=8.6 Hz, 1H), 7.71 (d, J=10.0 Hz, 1H), 8.11 (d, J=8.7 Hz, 1H), 8.71 (d, J=8.7 Hz, 1H).

FAB-MS (Li), m/z 1113.5 (MLi)⁺

The (bis)-trifluoroacetate salt from above was dissolved in H₂O and the solution passed through a Bio-Rad AG2-X8 (Cl⁻) polyprep column washing with additional water. The product-containing eluate was lyophilized to give the above compounds as the (bis)-hydrochloride salt. Lyophilization of the fractions containing the major product provided epi-product ¹H NMR (400 MHz, CD₃OD) δ3.02 (m, 1H), 3.14 (m, 3H), 4.16 (m, 1H), 5.10 (dd, 1H), 6.76 (d, 2H), 7.14 (d, 2H).

FAB-MS (Li), m/z 1113.9 (MLi)⁺

EXAMPLE 2

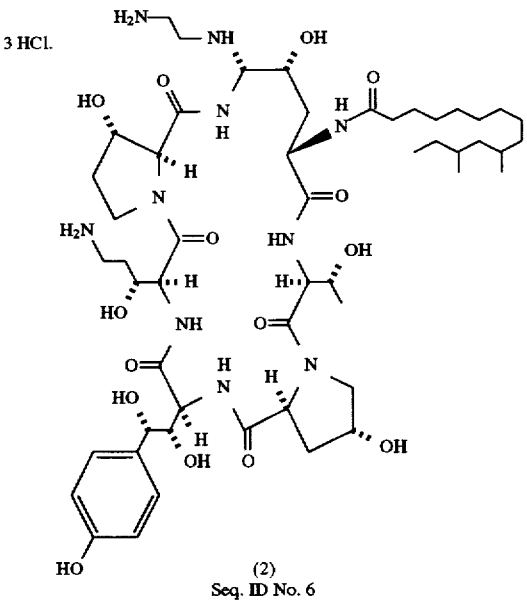

(2)
Seq. ID No. 6

Part A. Preparation of Intermediate Sulfone (Seq. ID No. 36)

The starting compound, Compound A-6 R'=DMTD (Seq. ID No. 21), was prepared as described for such compound in the section entitled Preparation of Starting Materials.

Compound A-6 was then converted to the epi-thio compound Compound B-6 (Seq ID. No. 36) in a manner similar to that described in Part A of Example 1.

To a stirred solution of 285 mg (0.241 mmol) of Compound B-6 in 14 mL of 1:1 acentonitrile/water was added "OXONE" (162 mg equivalent to 0.530 mmol of potassium hydrogen persulfate). After a period of 45 minutes, the solution was diluted with an equal volume of water and chromatographed. Reverse-phase (C18) flash column chromatography eluting with 30–45% acetonitrile/water (0.1% trifluoroacetic acid) in 5% step gradients was followed by lyophilization of the product-containing fractions to provide 212 mg of the epi-sulfone (Compound C-6 Seq ID. No. 36) Yield=84%.

$^1$H NMR (400 MHz, CD$_3$OD) δ3.08 (M, 2H), 3.46 (t, J=6.6 Hz, 2H), 3.68 (m), 5.05 (M), 6.77 (d, J=8.5 Hz, 2H), 7.15 (d, J=8.5 Hz, 2H)

FAB-MS (Li), m/z 1039.9

Part B. Preparation of the Product of Formula (2) (Compound I-6; R''=H; R'''=2-aminoethyl); Seq ID No. 6

To a stirred solution of Compound C-6 (prepared as described in Part A, 418 mg, 0.305 mmol) in 10 mL of anhydrous N,N-dimethylformamide was added ethylenediamine (183 mg, 3.05 mmol). After a period of 1 h, HPLC analysis (RP-C18, 35% CH$_3$CN/H$_2$O (0.1% CF$_3$COOH)) of the reaction mixture indicated complete conversion to two polar products in a ratio of 36:64. The reaction mixture was diluted with aqueous trifluoroacetic acid (190 mL H$_2$O, 0.4 mL CF$_3$COOH) and chromatographed. Reverse-phase (C18) flash column chromatography eluting with 10–25% acetonitrile/water (0.1% trifluoroacetic acid) in 5% step gradients was followed by lyophilization of the appropriate fractions to provide 111 mg of the product as the (tris)-trifluoroacetate salt:

Yield=25%

$^1$H NMR (400 MHz, CD$_3$OD) δ1.17 (d, J=6.2 Hz), 2.44 (dd, J=7.0 and 13.2 Hz, 1H), 2.7–3.0 (m, 4H), 3.06 (t, J=7.0 Hz, 2H), 3.82 (m, 3H), 3.97 (dd, J=11.2 and 3.2 Hz, 1H), 4.03 (m, 2H), 4.70 (d, J=2.3 Hz, 1H), 5.00 (d, J=3.3 Hz, 1H), 6.75 Hz (d, J=8.6 Hz, 2H), 7.11 (d, J=8.6 Hz, 2H)

FAB-MS (Li), m/z 1099.9 (MLi)$^+$, 1033.9

The (tris)-trifluoroacetate salt from above was dissolved in H$_2$O and the solution passed through a Bio-Rad AG2-X8 (Cl$^-$) polyprep column washing with additional water. The product-containing eluate was lyophilized to give 93 mg of the above compound as the (tris)-hydrochloride.

EXAMPLE 3

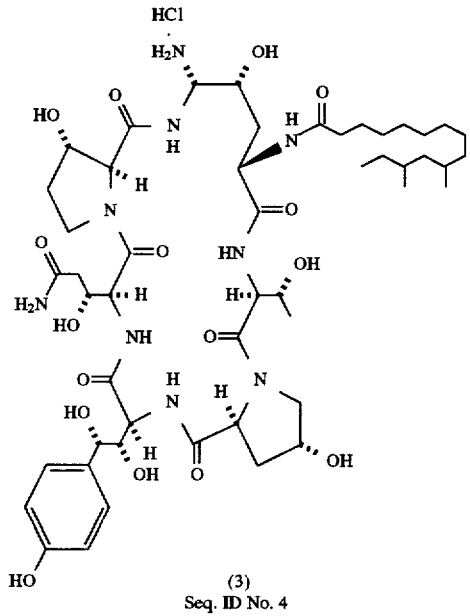

(3)
Seq. ID No. 4

Part A: Preparation of Azide (Seq. ID No. 49)

To a stirred solution of 297 mg, 0.257 mmol epi-sulfone (Example 1, Part B) in 10 milliliters of anhydrous dimethylformamide was added lithium azide (126 mg, 257 mmol). After a period of 1 hr, HPLC analysis (RP-18, 40% CH$_3$CN/H$_2$O (0.1% of CF$_3$COOH)) of the reaction mixture indicated complete conversion to a single substantially less polar product. Reverse phase (C18) flash column chromatography eluting with 30–65% acetonitrile/water in 5% step gradients was followed by lyophilization of the product-containing fractions to provide crude azide. Preparative HPLC (C18, 40–45% CH$_3$CN/H$_2$O (0.1% CF$_3$COOH) in one 5% step gradient) produced an azido compound, Compound D-4, (Seq. ID No. 49).

$^1$H NMR (400 MHz, CD$_3$OD) δ1.14 (d, J=6.1 Hz, 3H), 2.50 (dd, J=15.6 and 9.9 Hz, 1H), 2.84 (dd, J=15.6 and 3.3 Hz, 1H), 3.95 (dd, J=11.2 and 3.1 Hz, 1H), 4.05 (m, 2H), 4.56 (m, 3H), 4.98 (dd, J=8.5 and 3.5 Hz, 1H), 5.10 (dd, J=8.3 and 4.2 Hz, 1H), 5.26 (dd, J=8.5 and 2.2 Hz, 1H), 6.74 (d, J=8.6 Hz, 2H), 7.12 (d, J=8.6 Hz, 2H), 7.44 (d, J=8.3 Hz, 1H), 7.76 (d, J=9.9 Hz, 1H), 8.26 (d, J=8.1 Hz, 1H), 8.83 (d, J=8.7 Hz, 1H), 9.00 (d, J=8.5 Hz, 1H)

FAB-MS (Li), m/z 1096.9 (MH+Li)$^+$

IR (Nujol mull, cm$^{-1}$) 2110

Part B: Preparation of the Amine (Seq. ID No. 4)

A mixture of azido compound D-4, prepared in Part A, (137 mg, 0.126 mmol) and 10% Pd/C (137 mg) in glacial acetic acid (10 mL) was hydrogenated under balloon pressure for a period of 14 h. The catalyst was removed by filtration and the filtrate was lyophilized to obtain the crude amine. Purification by preparative HPLC (C18, 35–41% CH$_3$CN/H$_2$O (0.1% CF$_3$COOH) in 3% step gradients), followed by lyophilization of the appropriate fractions provided the aza compound, Compound I-1, R'', R'''=H (Seq. ID No. 1) as the trifluoroacetate salt: Yield=48%

$^1$H NMR (400 MHz, CD$_3$OD) δ1.13 (d, J=6.1 Hz, 3H), 2.49 (dd, J=15.6 and 9.8 Hz, 1H), 2.81 (dd, J=15.6 and 3.4 Hz, 1H), 3.97 (dd, J=11.1 and 3.1 Hz, 1H), 4.03 (m, 1H), 4.11 (m, 1H), 4.47 (dd, J=11.7 and 5.5 Hz, 1H), 4.57 (m, 2H), 5.00 (m, 1H), 5.10 (m, 1H), 5.14 (d, J=2.2 Hz, 1H), 6.74 (d, J=8.6 Hz, 2H), 7.12 (d, J=8.6 Hz, 2H), 7.42 (d, J=8.3 Hz, 1H), 8.89 (d, J=8.8 Hz, 1H)

FAB-MS(Li), m/z 1071.0 (MLi)$^+$

The trifluoroacetate was dissolved in H$_2$O and the solution passed through a Bio-Rad AG2-X8 (Cl$^-$) polyprep column, washing with additional water. The product-containing eluate was lyophilized to obtain 66 mg of compound I-4, R'', R'''=H (Seq ID No. 1) as the hydrochloride.

In the following experiments, Solvent A=95% water/5% acetonitrile/0.1% trifluoroacetic acid and Solvent B=95% acetonitrile/5% water/0.1% trifluoroacetic acid. When the expression "in vacuo" or "rotovaped" is used, it refers to removal of solvent on a rotary evaporator.

EXAMPLE 4

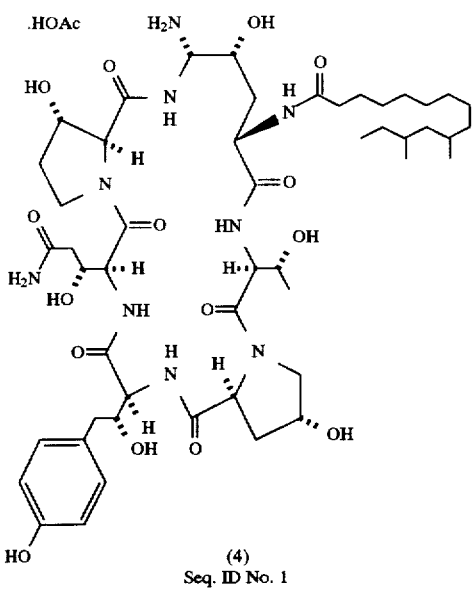

(4)
Seq. ID No. 1

A. Preparation of Intermediate Azide Compound D-1 (Seq ID No. 46)

Pneumocandin $B_0$ (Compound A-4; Seq ID No. 19) (5.00 g, 4.69 mmol) was dissolved in 2M $LiClO_4$-diethyl ether at room temperature. Trifluoroacetic acid (2.50 ml) was added to the stirring solution followed by triethylsilane (5.00 ml). The heterogeneous mixture was stirred rapidly for 6 hours after which time little or no starting pneumocandin $B_0$ was detectable by analytical HPLC (C18 "ZORBAX", 45% Solvent A/55% Solvent B/0.1% TFA, 1.5 ml/min). The mixture was poured into 200 ml of distilled water, filtered and air dried. The wet solid was stirred with diethyl ether, filtered and air dried to obtain 5.6 g of crude monoreduced pneumocandin $B_0$. (Compound A-1; Seq ID No. 16).

The crude isolate from above was added, as a solid, to a preformed solution of $HN_3$ prepared by dissolving $NaN_3$ (3.06 g, 47.0 mmol) in 100 ml of trifluoroacetic acid with cooling. After stirring at room temperature for 30 minutes, the reaction mixture was poured into 350 ml of distilled water and stirred for 15 minutes. The precipitate was filtered, dissolved in methanol and the solvent removed in vacuo. The residual water was removed by azeotropic removal with 100% ethanol. The final solid was subjected to high vacuum to remove volatiles. The mixture was purified in two equal batches by preparative HPLC (C18 "DELTAPAK", 60 ml/min, 48 ml fractions) using a step gradient elution from 70% A/30% B to 50% A/50% B. The appropriate fractions were combined (determined by UV monitoring at λ=220 and 277 nm). Impure fractions were combined and reprocessed in a similar fashion as described above. A total of 1.78 g (35% yield) of azide D-1 (Seq ID No. 46) was obtained in this manner.

$^1$H NMR (400 MHz, $CD_3OD$): δ7.02 (d, 2H), 6.69 (d, 2H), 5.30 (d, 1H), 5.11 (d, 1H), 4.98 (d, 1H), 2.74 (dd, 1H), 1.13 (d, 3H).

FAB-MS (Li), m/z 1081 $(MH+Li)^+$.

B. Preparation of Amine of Formula (4) Compound I-1 ($R''$, $R'''$=H (Seq ID No. 1)

The purified azide compound D-1 prepared above (1.50 g) was dissolved in 40 ml of methanol. 33% Aqueous acetic acid (15 ml) was added followed by 0.20 g of 10% Pd-C, then the reaction vessel was flushed with $N_2$. The atmo- sphere inside the flask was replaced with $H_2$ and the mixture was stirred rapidly under an atmosphere of $H_2$ for 3 hours. The suspension was filtered through a 0.2 μm frit and the clear solution was concentrated to dryness in vacuo. The residue was dissolved in approximately 20 ml of distilled water, frozen and lyophilized to obtain 1.47 g (95%) of the desired amine compound (Seq ID No. 1) as a white solid.

$^1$H NMR (400 MHz, $CD_3OD$): δ7.02 (d, 2H), 6.69 (d, 2H), 5.09 (d, 1H), 5.01 (d, 1H), 2.77 (dd, 1H), 1.15 (d, 3H).

FAB-MS (Li), m/z 1055 $(MH+Li)^+$

EXAMPLE 5

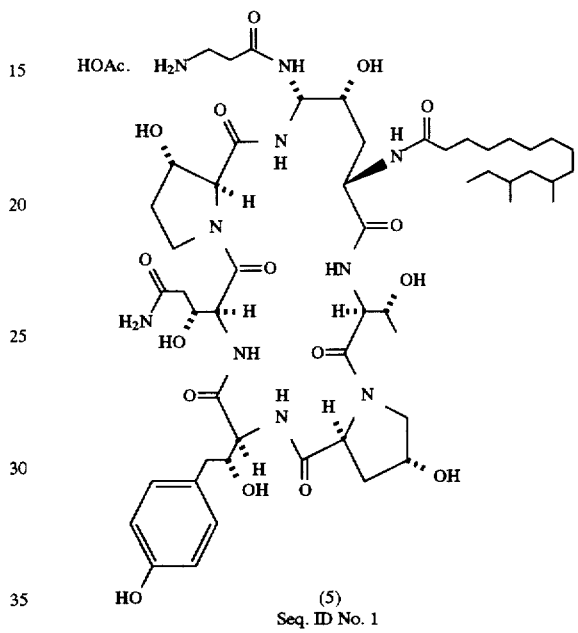

(5)
Seq. ID No. 1

A. Preparation of Intermediate Benzyloxycarbonyl Compound (Seq ID No. 1)

The amine of formula (4) from Example 4 (200 mg, 0.180 mmol) and pentafluorophenyl N-benzyloxycarbonyl-3-aminopropanoate were dissolved in 1 ml of dimethylformamide. Diisopropylethylamine (0.035 ml, 0.198 mmol) was added and the mixture was stirred at ambient temperature for 1 hour. The reaction mixture was diluted with 2 mls methanol and purified by preparative HPLC (C18 "DELTAPAK", step gradient: 70% A/30% B to 48% A/52% B, 48 ml fractions). The appropriate fractions as determined by UV absorbance (220, 277 nm) were combined, frozen and lyophilized to produce 100 mg (44%) of the desired intermediate.

$^1$H NMR (400 MHz, $CD_3OD$): δ7.32 (m, 5H), 7.01 (d, 2H), 6.69 (d, 2H), 5.64 (bd, 1H), 1.18 (d, 3H).

FAB-MS (Li), m/z 1259 $(MLi)^+$

B. Preparation of 3-aminopropanoyl Compound of formula (5); Compound I-1 $R''$=H; $R'''$=$CO(CH_2)_2NH_2$ (Seq ID No. 1)

Benzyloxycarbonyl compound from Part A (94 mg, 0.075 mmol) was dissolved in a mixture of 3 ml methanol, 1 ml of water and 0.2 ml of acetic acid. 10% Pd-C (48 mg) was added and the vessel was flushed with $N_2$ gas. Next, the vessel was flushed with $H_2$ and the mixture was stirred vigorously under 1 atm $H_2$ for 2 hours. Removal of the volatiles in vacuo gave a solid. The solid was dissolved in about 4 ml of 50% aqueous acetonitrile, frozen and lyophilized to give 80 mg (91%) of the desired compound of formula (5) as a white solid.

$^1$H NMR (400 MHz, CD$_3$OD): δ7.01 (d, 2H), 6.69 (d, 2H), 6.67 (d, 1H), 5.10 (d, 1H), 4.99 (d, 1H), 3.12 (m, 2H), 1.91 (s, 3H), 1.17 (d, 3H).

FAB-MS (Li), m/z 1125 (MLi)$^+$

EXAMPLE 6

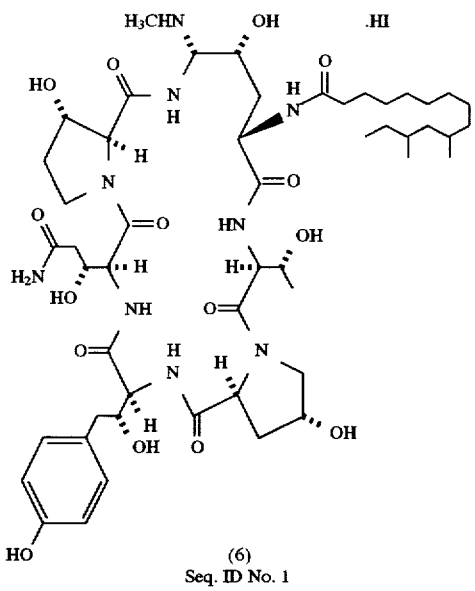

(6)
Seq. ID No. 1

Preparation of N-Methylamino Compound of formula (6); Compound I-1 (R''=H; R'''=CH3) (Seq ID No. 1)

The amine of formula (5) from Example 5 (45.6 mg, 0.135 mmol) was dissolved in 0.5 ml of dry dimethylformamide. Iodomethane (0.021 ml, 0.338 mmol) was added followed by diisopropylethylamine (0.0824 ml, 0.473 mmol). After stirring at ambient temperature for 24 hours, the volatiles were removed in vacuo and the crude product was analyzed by mass spectrometry.

FAB-MS (Li), m/z 1068 (MLi)$^+$

EXAMPLE 7

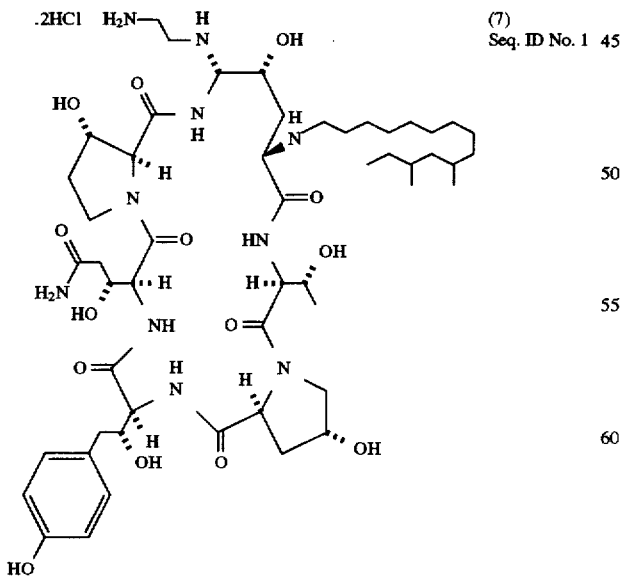

(7)
Seq. ID No. 1

A. Preparation of Intermediate Nitrile(N-Cyanomethyl) Compound I-1; R''=H; R'''=CH$_2$CN (Seq ID No. 1)

The amine compound prepared as described in Example 4 (500 mg, 0.451 mmol) was dissolved in 3 ml of dry dimethylformamide. Bromoacetonitrile that had been prepurified by passing through a small plug of magnesium sulfate-sodium bicarbonate (0.063 ml, 0.902 mmol), was added followed by diisopropylethylamine (0.157 ml, 0.902 mmol). The clear reaction mixture was stirred for 12 hours and then diluted with a small volume of water. The solution was purified by preparative HPLC (C18 "DELTAPAK", step gradient: 70% A/30% B to 47% A/53% B, 48 ml fractions). The appropriate fractions, as determined by UV absorbance at 220 and 277 nm, were pooled, frozen and lyophilized to yield 338 mg (62%) of the desired intermediate cyanomethyl compound as a water insoluble solid.

$^1$H NMR (400 MHz, CD$_3$OD): δ7.01 (d, 2H), 6.69 (d, 2H), 5.12 (dd, 1H), 5.01 (dd, 1H), 3.80 (s, 2H), 2.76 (dd, 1H), 1.15 (d, 3H).

FAB-MS (Li), m/z 1094 (MH+Li)$^+$

B. Preparation of N-aminoethyl Compound of formula (7); Compound I-1; R''=H, R'''=(CH$_2$)$_2$NH$_2$ (Seq ID No. 1)

The nitrile (cyanomethyl) compound prepared above (300 mg, 0.249 mmol) was dissolved in 5.0 ml of methanol. Next, nickel (II) chloride hexahydrate (237 mg, 0.997 mmol) was added. Sodium borohydride (189 mg, 4.99 mmol) was added to the solution in three portions. A black precipitate formed immediately and the mixture was stirred for 15 minutes at ambient temperature. The heterogeneous mixture was diluted with about 20–40 ml of water and approximately 10–15 ml of 2N HCl was added. Stirring was continued for 45 minutes until the black precipitate had dissolved and a blue-green solution remained. Purification was accomplished by preparative HPLC (C18 "DELTAPAK", step gradient: 70% A/30% B to 55% A/45% B, 48 ml fractions). The appropriate fractions, as determined by UV absorbance at 220 and 277 nm, were pooled, frozen and lyophilized to yield 180 mg (55%) of the desired product. The material was dissolved in 30 ml of water and passed through an ion exchange column (Cl$^-$ form), rinsing with distilled water. The solution was frozen and lyophilized to obtain 149 mg (94% recovery) of the desired aminoethyl compound of formula (7) Seq ID NO. 1 as a white solid.

$^1$H NMR (400 MHz, CD$_3$OD): δ7.01 (d, 2H), 6.69 (d, 2H), 5.11 (dd, 1H), 5.07 (dd, 1H), 1.14 (d, 3H).

FAB-MS (Li), m/z 1098 (MH+Li)$^+$

EXAMPLE 8

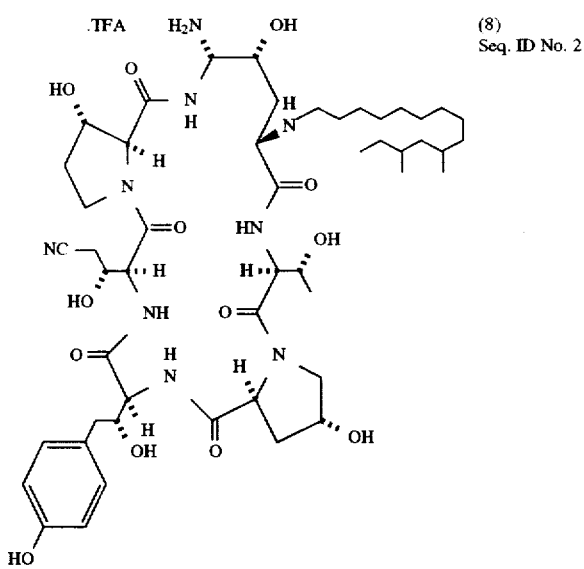

(8)
Seq. ID No. 2

A. Preparation of Intermediate Azide Compound (Seq ID No. 47)

Pneumocandin $B_0$ nitrile (Seq ID No. 20) (2.00 g, 1.91 mmol) was dissolved in 24 ml of 2M $LiClO_4$-diethyl ether. Triethylsilane (2.00 ml) followed by trifluoroacetic acid (1.00 ml) was added and the mixture was rapidly stirred at ambient temperature for 6 hours. The mixture was poured into 300 ml of water, stirred for 15 minutes and filtered. The filter cake was dissolved in a minimal amount of methanol and the solvent removed in vacuo. The residual water was azeotroped with 100% ethanol and the residue was subjected to high vacuum overnight to remove volatiles to obtain a product (Seq ID No. 17) mono-reduced at the benzylic carbon.

The crude solid from above and sodium azide (1.26 g, 19.4 mmol) were placed in a roundbottom flask equipped with a stirring bar and cooling bath. Trifluoroacetic acid (50 ml) was slowly added, the cooling bath was removed and the mixture was stirred for 2 hours. It was poured into 300 ml of water and filtered. The solid was dissolved in methanol, rotovaped and pumped under high vacuum to remove volatiles. The crude material was purified by preparative HPLC (C18 "DELTAPAK", step gradient: 55% A/45% B to 45% A/55% B, 56 ml fractions). The appropriate fractions, as determined by UV absorbance at 220 and 277 nm, were pooled, frozen and lyophilized to yield 0.59 g (29%) of the desired intermediate azide (Seq ID No. 47).

$^1$H NMR (400 MHz, $CD_3OD$): δ7.00 (d, 2H), 6.69 (d, 2H), 5.34 (d, 1H), 5.07 (d, 1H), 5.00 (m, 1H), 2.88 (dd, 1H), 1.17 (d, 3H).

FAB-MS (Li), m/z 1036 $(M-N_2+Li)^+$

B. Preparation of Compound of Formula (8) (Seq ID No. 48)

The purified azide from Part A (0.15 g, 0.142 mmol) was dissolved in a mixture of 4 ml methanol, 1 ml water and 0.5 ml of acetic acid. 10% Pd—C (50 mg) was added to the solution. The reaction flask was flushed with $N_2$, then with $H_2$. The mixture was rapidly stirred at ambient temperature for 5 hours under 1 atmosphere of $H_2$. Subsequent filtration through a 0.2 μm frit and removal of the volatiles in vacuo produced 0.124 g (80%) of the desired compound of formula (8) Compound I-2; R″, R‴=H; R′=DMTD (Seq ID No. 2) as a white solid.

$^1$H NMR (400 MHz, $CD_3OD$): δ7.00 (d, 2H), 6.69 (d, 2H), 5.04 (d, 1H), 5.01 (m, 1H), 2.79 (dd, 1H), 1.18 (d, 3H).

FAB-MS (Li), m/z 1037 $(MH+Li)^+$

EXAMPLE 9

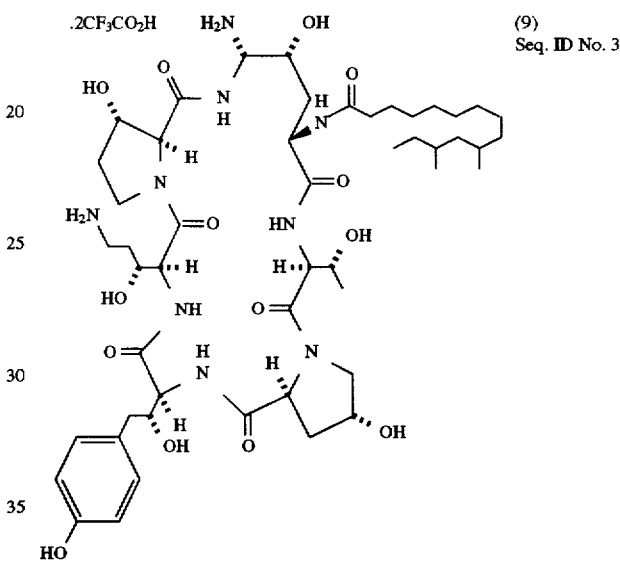

(9)
Seq. ID No. 3

Preparation of Amine Compound of Formula (9) (Seq ID No. 3).

The purified azide-nitrile from Example 8, Part A (44 mg, 0.0416 mmol) was dissolved in 1.5 ml of methanol followed by $CoCl_2.6H_2O$ (59 mg, 0.25 mmol). Next, $NaBH_4$ (8×12 mg, 2.50 mmol) was added cautiously in portions. The black, heterogeneous reaction mixture was stirred for 30 minutes at ambient temperature. The reaction was quenched by adding about 1.5 ml of 2N HCl and enough acetic acid to dissolve the precipitate. The pale solution was diluted with 3 ml of water and purified by preparative HPLC (C18 "ZORBAX", step gradient: 70% A/30% B to 60%A/40% B, 15 ml/min, 15 ml fractions). The appropriate fractions as determined by UV absorbance at 210 and 277 nm, were pooled, frozen and lyophilized to obtain 38 mg (72%) of the desired compound of formula (9) as a white solid.

$^1$H NMR (400 MHz, $CD_3OD$): δ6.99 (d, 2H), 6.70 (d, 2H), 5.11 (d, 1H), 5.0 (m, 1H), 3.05 (m, 2H), 1.17 (d, 3H).

FAB-MS (Li), m/z 1041 $(MH+Li)^+$

EXAMPLE 10

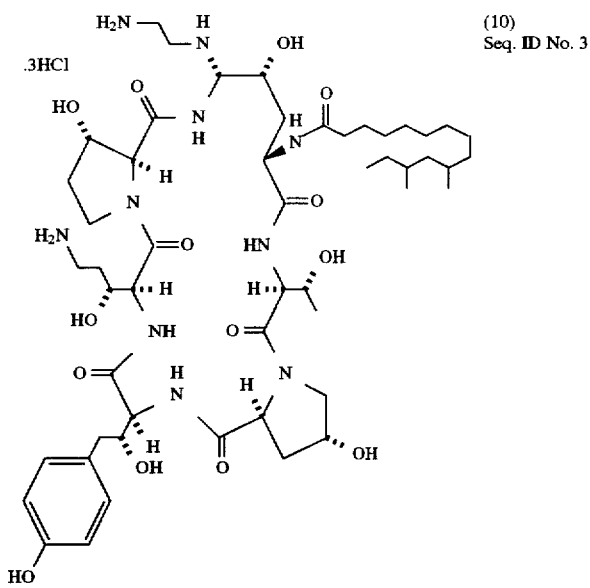

(10)
Seq. ID No. 3

A. Preparation of Intermediate Bis-nitrile Compound (Compound I-2; R''=H; R'''=CH$_2$CN; R'=DMTD) (Seq ID No. 2)

The nitrile-amine compound of Example 8 Part B (500 mg, 0.459 inmol) was dissolved in 3 ml of dry dimethylformamide. Bromoacetonitrile that had been prepurified by passing through a small plug of magnesium sulfate-sodium bicarbonate (0.064 ml, 0.917 mmol), was added followed by diisopropylethylamine (0.155 ml, 0.917 mmol). The reaction mixture was stirred at ambient temperature for 18 hours. It was diluted with water and purified by preparative HPLC (C18 "DELTAPAK", 60 ml/min, step gradient: 70% A/30% B to 50% A/50% B, 48 ml fractions). The appropriate fractions, as determined by UV absorbance at 220 and 277 nm, were pooled, frozen and lyophilized to obtain 198 mg (36%) of the desired Compound I-2; R''=H; R'''=CH$_2$CN $^1$H NMR (400 MHz, CD$_3$OD): δ7.00 (d, 2H), 6.69 (d, 2H), 5.08 (dd, 1H), 5.01 (dd, 1H), 3.73 (s, 2H), 2.79 (dd, 1H), 1.18 (d, 3H).

FAB-MS (Li), m/z 1076 (MH+Li)$^+$

B. Preparation of Compound of formula (10) (Seq ID No. 3)

The bis-nitrile from Part A (184 mg, 0.155 mmol) was dissolved in 3 ml of methanol. NiCl$_2$.6H$_2$O (148 mg, 0.621 mmol) was added in the methanol and NaBH$_4$ (117 mg, 3.1 mrnol) was added in three portions. After 5 minutes, CoCl$_2$.6H$_2$O (148 mg, 0.621 mmol) was added and stirred about 1 minute. An additional 117 mg of NaBH$_4$ was added and stirring was continued for 15 minutes. Another 60 mg portion of NaBH$_4$ was added to drive the reaction to completion. The mixture was diluted with water, acidified with 2N HCl and stirred until the black precipitate dissolved. Purification by preparative HPLC (C18 "ZORBAX", 15 ml/min, step gradient: 70% A/30% B to 55% A/45% B, 22.5 ml fractions, 220, 277 nm) gave after lyophilization a solid. The solid was dissolved in water and passed through an ion exchange column (Cl$^-$ form), frozen and lyophilized to give 81.1 mg (44%) of the desired compound of formula (10) (Compound I-3 (Seq ID No. 3) as a white solid.

$^1$H NMR (400 MHz, CD$_3$OD): δ7.00 (d, 2H), 6.70 (d, 2H), 3–3.3 (m, 6H), 1.18 (d, 3H).

FAB-MS (Li), m/z 1084 (MH+Li)$^+$

EXAMPLE 11–14

In operations carried out in a manner similar to that described in Example 4, the appropriate cyclopeptide natural products or modified natural products obtained as described hereinafter on preparation of starting materials are in separate operations dissolved in LiClO$_4$-diethyl ether and to it is added with stirring trifluoroacetic acid and triethylsilane for 5 to 10 hours. The mixture is then poured into water, filtered, and the solid stirred with diethyl ether, then filtered and air dried to obtain cyclopeptide in which R$_1$ has been reduced to H.

The monoreduced compound is added to a preformed solution of HN$_3$ (from NaN$_3$ and trifluoroacetic acid) with cooling and stirred at room temperature form 30 minutes to one hour and then poured into water to obtain the azide product which is recovered in the manner previously described.

The azide is hydrogentated as previously described using Pd/C as catalyst and the product is recovered from the filtrate after separation of the catalyst.

The products obtained in this manner are as follows:

| Example | R$_1$ | R$_2$ | R$_3$ | NR$^{II}$ | R$^{III}$ | R$^I$ | Seq. ID No. |
|---|---|---|---|---|---|---|---|
| 11 | H | H | CH$_2$CONH$_2$ | H | H | C$_6$H$_4$OC$_8$H$_{17}$ | 12 |
| 12 | H | H | CH$_2$CN | H | H | C$_6$H$_4$OC$_8$H$_{17}$ | 13 |
| 13 | H | H | CH$_2$CH$_2$NH$_2$ | H | H | C$_6$H$_4$OC$_8$H$_{17}$ | 14 |
| 14 | H | CH$_3$ | CH$_3$ | H | H | C$_6$H$_4$OC$_8$H$_{17}$ | 15 |

EXAMPLES 15–17

In operations carried out in a manner similar to that described in Example 7, the compounds of Examples 11, 13 and 14, are dissolved in dimethylformamide and added thereto are purified bromoacetonitrile followed by diisopropylethylamine and the mixture stirred from twelve to eighteen hours to produce a nitrile (an N-cyanomethyl) compound. The latter is purified by preparative HPLC.

The nitrile is dissolved in methanol and reduced chemically employing nickel (II) chloride and sodium borohydride to obtain animoethyl substituted compound as follows:

| Example | R$_1$ | R$_2$ | R$_3$ | NR$^{II}$ | R$^{III}$ | R$^I$ | Seq ID No. |
|---|---|---|---|---|---|---|---|
| 15 | H | H | CH$_2$CONH$_2$ | H | CH$_2$CH$_2$NH$_2$ | C$_{10}$H$_6$OC$_8$H$_{17}$ | 12 |
| 16 | H | H | (CH$_2$)$_2$NH$_2$ | H | CH$_2$CH$_2$NH$_2$ | C$_{10}$H$_6$OC$_8$H$_{17}$ | 14 |
| 17 | H | H | CH$_3$ | H | CH$_2$CH$_2$NH$_2$ | C$_{10}$H$_6$OC$_8$H$_{17}$ | 15 |

EXAMPLES 18–21

In operations carried out in a manner similar to that described in Example 1, 2 and 3, compounds having the substituents below may be prepared:

| Example | $R_1$ | $R_2$ | $R_3$ | $NR^{II}$ | $R^{III}$ | $R^1$ | Seq ID No. |
|---|---|---|---|---|---|---|---|
| 18 | OH | $CH_3$ | $CH_2CONH_2$ | H | $CH_2CH_2NH_2$ | DMTD | 7 |
| 19 | OH | $CH_3$ | $CH_2CH_2NH_2$ | H | $CH_2CH_2NH_2$ | DMTD | 8 |
| 20 | OH | OH | $CH_2CONH_2$ | H | $CH_2CH_2NH_2$ | DMTD | 9 |
| 21 | OH | OH | $CH_2CH_2NH_2$ | H | $CH_2CH_2NH_2$ | DMTD | 14 |

EXAMPLES 22–25

In operations carried out in a manner similar to that described in Example 1, the following compounds are prepared:

| Example | $R_1$ | $R_2$ | $R_3$ | $NR_{II}$ | $R_{III}$ | $R_1$ | Seq ID No. |
|---|---|---|---|---|---|---|---|
| 22 | OH | $CH_3$ | $CH_3$ | H | $CH_2CH_2NH_2$ | $C_6H_4OC_8H_{17}$ | 10 |
| 23 | OH | $CH_3$ | H | H | $CH_2CH_2NH_2$ | $C_6H_4OC_8H_{17}$ | 11 |
| 24 | OH | H | $CH_2CH_2NH_2$ | H | $(CH_2)_3NH_2$ | DMTD | 6 |
| 25 | OH | H | $CH_2CH_2NH_2$ | H | $CH_2CH_2NH_2$ | DMTD | 6 |

EXAMPLE 26

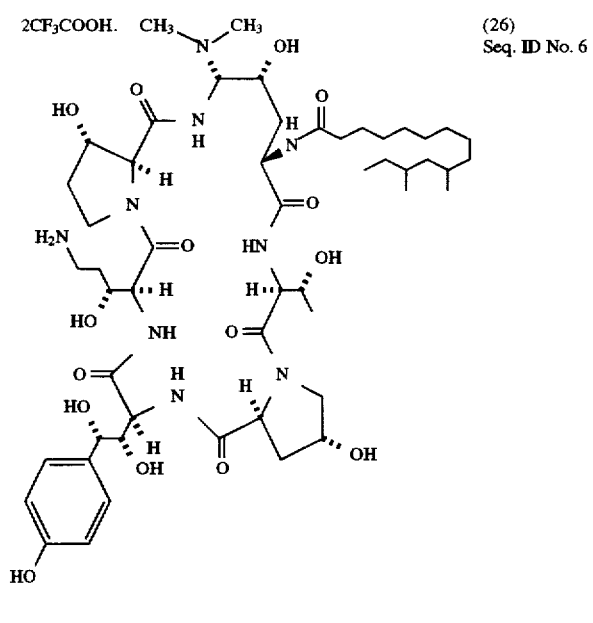

(26)
Seq. ID No. 6

The above compound is prepared in a manner similar to that described in Example 2, Part B, substituting dimethylamine for ethylenediamine to obtain a compound of M.W.= 1334.43.

EXAMPLE 27

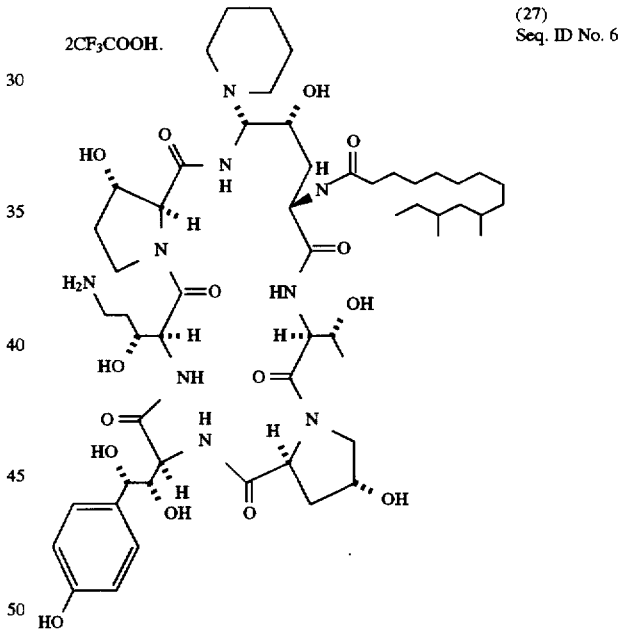

(27)
Seq. ID No. 6

The above compound is prepared in a manner similar to that in Example 26, substituting piperidine for dimethylamine to obtain a compound of M.W. 1374.

EXAMPLE 28

1000 compressed tablets each containing 500 mg of the compound of formula (2), [Compound I-6 ($R''$=H; $R'''$=2-aminoethyl) Seq ID No 6.], are prepared from the following formulation:

| Compound | Grams |
| --- | --- |
| Compound of Example 2 | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

EXAMPLE 29

1000 hard gelatin capsules, each containing 500 mg of the same compound are prepared from the following formulation:

| Compound | Grams |
| --- | --- |
| Compound of Example 2 | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE 30

An aerosol composition may be prepared having the following formulation:

| | Per Canister |
| --- | --- |
| Compound of Example 2 | 24 mg |
| Lecithin NF Liquid Concd. | 1.2 mg |
| Trichlorofluoromethane, NF | 4.026 g |
| Dichlorodifluoromethane, NF | 12.15 g |

EXAMPLE 31

250 milliliters of an injectible solution may be prepared by conventional procedures having the following formulation:

| Dextrose | 12.5 g |
| --- | --- |
| Water | 250 ml |
| Compound of Example 4 | 400 mg |

The ingredients are blended and thereafter sterilized for use.

PREPARATION OF STARTING MATERIALS

A-4 when $R'$ is DMTD may be produced by cultivating *Zalerion arboricola* ATCC 206868 in nutrient medium with mannitol as the primary source of carbon as described in U.S. Pat. No. 5,021,342 Jun. 4, 1991.

A-7 when $R'$ is DMTD may be produced by cultivating *Zalerion arboricola* ATCC 20868 in nutrient medium as described in U.S. Pat. No. 4,931,352, Jun. 5, 1990.

A-10 when $R'$ is linoleyl may be produced by cultivating *Asperzillus nidulans* NRRL 11440 in nutrient medium as described in U.S. Pat. No. 4,288,549, Sep. 8, 1981.

A-11 when $R'$ is 11-methyltridecyl may be produced by cultivating *Aspergillus sydowi* in nutrient medium as described in J. Antibiotics XL (No. 3) p 28 (1987).

A-12 may be produced by cultivation of *Zalerion arboricola* ATCC 20958 in nutrient medium as described in copending application Ser. No. 07/630,457, filed Dec. 19, 1990 (Atty Docket No. 18268), now U.S. Pat. No. 5,306,708.

Compounds in which $R_1$ is H may be produced as described in Example 4, Part A.

Compounds in which $R_3$ is $CH_2CN$ such as A-2, A-5 and A-8 may be produced by the reaction of a compound having a carboxamide group in the corresponding position with excess cyanuric chloride in an aprotic solvent. Molecular sieves may be employed in this reaction. After completion of the reaction, the sieves, if employed, are removed, and the filtrate concentrated to obtain the nitrile compound as more fully described in copending application, Ser No. 936,434, Sep. 3, 1992.

Compounds in which $R_3$ is $CH_2CH_2NH_2$ such as A-3, A-6 and A-9 may be produced by either a chemical or catalytic reduction of the nitrile. It is conveniently carried out employing large molar excess of sodium borohydride with cobaltous chloride as more fully described in copending application Ser. No. 936,558, Sep. 3, 1992.

Starting materials in which $R'$ is a different group from that of the natural product may be obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as described in Experentia 34, 1670 (1978) or U.S. Pat. No. 4,293,482, recovering the deacylated cyclopeptide, and thereafter acylating the deacylated cyclopepetide by mixing together with an appropriate active ester $R'COX$ to obtain Compound A with the desired acyl group.

What is claimed is:

1. A compound having the formula

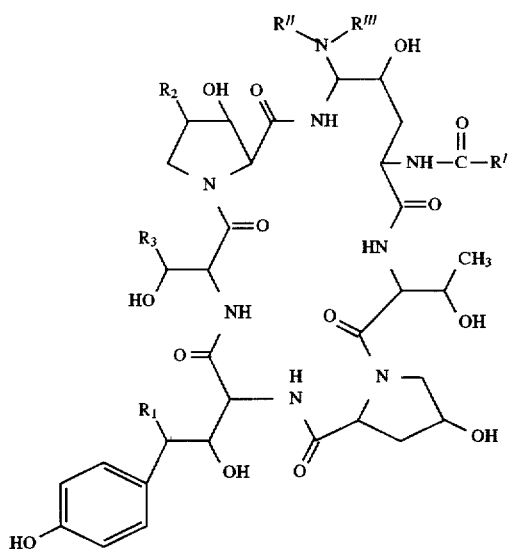

wherein:
$R_1$ is H or OH;
$R_2$ is H, $CH_3$ or OH;
$R_3$ is H, $CH_3$, $CH_2CN$, $CH_2CH_2NH_2$ or $CH_2CONH_2$;
$R'$ is $C_9$–$C_{21}$ alkyl, $C_9$–$C_{21}$ alkenyl, $C_1$–$C_{10}$ alkoxyphenyl or $C_1$–$C_{10}$ alkoxynaphthyl;
$R''$ is H, $C_1$–$C_4$ alkyl, $C_3$–$C_4$ alkenyl, $(CH_2)_{2-4}OH$, $(CH_2)_{2-4}NR^{IV}R^V$, $CO(CH_2)_{1-4}NH_2$;
$R'''$ is H, $C_1$–$C_4$ alkyl, $C_3$–$C_4$ alkenyl, $(CH_2)_{2-4}$ OH, $(CH_2)_{2-4}$ $NR^{IV}R^V$, or
$R''$ and $R'''$ taken together are —$(CH_2)_4$—, —$(CH_2)_5$—, —$(CH_2)_2O(CH_2)_2$— or —$(CH_2)_2$—NH—$(CH_2)_2$—;
$R^{IV}$ is H or $C_1$–$C_4$ alkyl,
$R^V$ is H or $C_1$–$C_4$ alkyl; and acid addition salts thereof.

2. An antimicrobial composition comprising a compound of claim 1 in admixture with a pharmaceutically acceptable carrier.

3. A method for treatment of mycotic infections comprising administering to mammalian subject in need of treatment, an antimycotic amount of a compound of claim 1.

4. A method for treatment of pneumocystis pneumonia in immune-compromised patients comprising administering a therapeutically effective amount of a compound of claim 1.

* * * * *

SEQUENCE LISTING ( 1 ) GENERAL INFORMATION:

( i i i ) NUMBER OF SEQUENCES: 60

( 2 ) INFORMATION FOR SEQ ID NO:1:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 1:

Xaa  Thr  Xaa  Xaa  Xaa  Xaa
        1                         5

( 2 ) INFORMATION FOR SEQ ID NO:2:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 2:

Xaa  Thr  Xaa  Xaa  Xaa  Xaa
        1                         5

( 2 ) INFORMATION FOR SEQ ID NO:3:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 3:

Xaa  Thr  Xaa  Xaa  Xaa  Xaa
        1                         5

( 2 ) INFORMATION FOR SEQ ID NO:4:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 4:

Xaa  Thr  Xaa  Xaa  Xaa  Xaa
        1                         5

( 2 ) INFORMATION FOR SEQ ID NO:5:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 5:

```
Xaa  Thr  Xaa  Xaa  Xaa  Xaa
1                  5
```

( 2 ) INFORMATION FOR SEQ ID NO:6:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 6:

```
Xaa  Thr  Xaa  Xaa  Xaa  Xaa
1                  5
```

( 2 ) INFORMATION FOR SEQ ID NO:7:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 7:

```
Xaa  Thr  Xaa  Xaa  Xaa  Xaa
1                  5
```

( 2 ) INFORMATION FOR SEQ ID NO:8:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 8:

```
Xaa  Thr  Xaa  Xaa  Xaa  Xaa
1                  5
```

( 2 ) INFORMATION FOR SEQ ID NO:9:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 9:

```
Xaa  Thr  Xaa  Xaa  Xaa  Xaa
1                  5
```

( 2 ) INFORMATION FOR SEQ ID NO:10:

( i ) SEQUENCE CHARACTERISTICS:
        ( A ) LENGTH: 6
        ( B ) TYPE: AMINO ACID
        ( C ) STRANDEDNESS: Not Relevant (D) TOPOLOGY: CIRCULAR (ii) MOLECULE TYPE:
    (A) DESCRIPTION: PEPTIDE (xi) SEQUENCE DESCRIPTION: SEQ ID NO: 10:

```
Xaa Ser Xaa Xaa Xaa Xaa
 1               5
```

(2) INFORMATION FOR SEQ ID NO:11:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 11:

```
Xaa Thr Xaa Xaa Xaa Xaa
 1               5
```

(2) INFORMATION FOR SEQ ID NO:12:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 12:

```
Xaa Thr Xaa Xaa Xaa Xaa
 1               5
```

(2) INFORMATION FOR SEQ ID NO:13:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 13:

```
Xaa Thr Xaa Xaa Xaa Xaa
 1               5
```

(2) INFORMATION FOR SEQ ID NO:14:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 14:

```
Xaa Thr Xaa Xaa Xaa Xaa
 1               5
```

(2) INFORMATION FOR SEQ ID NO:15:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 15:

```
Xaa  Thr  Xaa  Xaa  Xaa  Xaa
 1                  5
```

( 2 ) INFORMATION FOR SEQ ID NO:16:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 16:

```
Xaa  Thr  Xaa  Xaa  Xaa  Xaa
 1                  5
```

( 2 ) INFORMATION FOR SEQ ID NO:17:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 17:

```
Xaa  Thr  Xaa  Xaa  Xaa  Xaa
 1                  5
```

( 2 ) INFORMATION FOR SEQ ID NO:18:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 18:

```
Xaa  Thr  Xaa  Xaa  Xaa  Xaa
 1                  5
```

( 2 ) INFORMATION FOR SEQ ID NO:19:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 19:

```
        Xaa  Thr  Xaa  Xaa  Xaa  Xaa
         1                5
```

( 2 ) INFORMATION FOR SEQ ID NO:20:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 20:

```
        Xaa  Thr  Xaa  Xaa  Xaa  Xaa
         1                5
```

( 2 ) INFORMATION FOR SEQ ID NO:21:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 21:

```
        Xaa  Thr  Xaa  Xaa  Xaa  Xaa
         1                5
```

( 2 ) INFORMATION FOR SEQ ID NO:22:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 22:

```
        Xaa  Thr  Xaa  Xaa  Xaa  Xaa
         1                5
```

( 2 ) INFORMATION FOR SEQ ID NO:23:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 23:

```
        Xaa  Thr  Xaa  Xaa  Xaa  Xaa
         1                5
```

( 2 ) INFORMATION FOR SEQ ID NO:24:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 24:

Xaa Thr Xaa Xaa Xaa Xaa
    1                   5

( 2 ) INFORMATION FOR SEQ ID NO:25:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 25:

Xaa Thr Xaa Xaa Xaa Xaa
    1                   5

( 2 ) INFORMATION FOR SEQ ID NO:26:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 26:

Xaa Thr Xaa Xaa Xaa Xaa
1                  5

( 2 ) INFORMATION FOR SEQ ID NO:27:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 27:

Xaa Thr Xaa Xaa Xaa Xaa
1           5

( 2 ) INFORMATION FOR SEQ ID NO:28:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 28:

Xaa Thr Xaa Xaa Xaa Xaa
1           5

( 2 ) INFORMATION FOR SEQ ID NO:29:

( i ) SEQUENCE CHARACTERISTICS:

( A ) LENGTH: 6
( B ) TYPE: AMINO ACID
( C ) STRANDEDNESS: Not Relevant
( D ) TOPOLOGY: CIRCULAR ( i i ) MOLECULE TYPE:
( A ) DESCRIPTION: PEPTIDE ( x i ) SEQUENCE DESCRIPTION: SEQ ID NO: 29:

Xaa Thr Xaa Xaa Xaa Xaa
1               5

( 2 ) INFORMATION FOR SEQ ID NO:30:

( i ) SEQUENCE CHARACTERISTICS:
( A ) LENGTH: 6
( B ) TYPE: AMINO ACID
( C ) STRANDEDNESS: Not Relevant
( D ) TOPOLOGY: CIRCULAR ( i i ) MOLECULE TYPE:
( A ) DESCRIPTION: PEPTIDE ( x i ) SEQUENCE DESCRIPTION: SEQ ID NO: 30:

Xaa Thr Xaa Xaa Xaa Xaa
1               5

( 2 ) INFORMATION FOR SEQ ID NO:31:

( i ) SEQUENCE CHARACTERISTICS:
( A ) LENGTH: 6
( B ) TYPE: AMINO ACID
( C ) STRANDEDNESS: Not Relevant
( D ) TOPOLOGY: CIRCULAR ( i i ) MOLECULE TYPE:
( A ) DESCRIPTION: PEPTIDE ( x i ) SEQUENCE DESCRIPTION: SEQ ID NO: 31:

Xaa Thr Xaa Xaa Xaa Xaa
1               5

( 2 ) INFORMATION FOR SEQ ID NO:32:

( i ) SEQUENCE CHARACTERISTICS:
( A ) LENGTH: 6
( B ) TYPE: AMINO ACID
( C ) STRANDEDNESS: Not Relevant
( D ) TOPOLOGY: CIRCULAR ( i i ) MOLECULE TYPE:
( A ) DESCRIPTION: PEPTIDE ( x i ) SEQUENCE DESCRIPTION: SEQ ID NO: 32:

Xaa Thr Xaa Xaa Xaa Xaa
1               5

( 2 ) INFORMATION FOR SEQ ID NO:33:

( i ) SEQUENCE CHARACTERISTICS:
( A ) LENGTH: 6
( B ) TYPE: AMINO ACID
( C ) STRANDEDNESS: Not Relevant
( D ) TOPOLOGY: CIRCULAR ( i i ) MOLECULE TYPE:
( A ) DESCRIPTION: PEPTIDE ( x i ) SEQUENCE DESCRIPTION: SEQ ID NO: 33:

Xaa Thr Xaa Xaa Xaa Xaa
1               5

( 2 ) INFORMATION FOR SEQ ID NO:34:

( i ) SEQUENCE CHARACTERISTICS:
      ( A ) LENGTH: 6
      ( B ) TYPE: AMINO ACID
      ( C ) STRANDEDNESS: Not Relevant
      ( D ) TOPOLOGY: CIRCULAR ( i i ) MOLECULE TYPE:
      ( A ) DESCRIPTION: PEPTIDE ( x i ) SEQUENCE DESCRIPTION: SEQ ID NO: 34:

Xaa  Thr  Xaa  Xaa  Xaa  Xaa
      1                  5

( 2 ) INFORMATION FOR SEQ ID NO:35:

( i ) SEQUENCE CHARACTERISTICS:
      ( A ) LENGTH: 6
      ( B ) TYPE: AMINO ACID
      ( C ) STRANDEDNESS: Not Relevant
      ( D ) TOPOLOGY: CIRCULAR ( i i ) MOLECULE TYPE:
      ( A ) DESCRIPTION: PEPTIDE ( x i ) SEQUENCE DESCRIPTION: SEQ ID NO: 35:

Xaa  Thr  Xaa  Xaa  Xaa  Xaa
      1                  5

( 2 ) INFORMATION FOR SEQ ID NO:36:

( i ) SEQUENCE CHARACTERISTICS:
      ( A ) LENGTH: 6
      ( B ) TYPE: AMINO ACID
      ( C ) STRANDEDNESS: Not Relevant
      ( D ) TOPOLOGY: CIRCULAR ( i i ) MOLECULE TYPE:
      ( A ) DESCRIPTION: PEPTIDE ( x i ) SEQUENCE DESCRIPTION: SEQ ID NO: 36:

Xaa  Thr  Xaa  Xaa  Xaa  Xaa
      1                  5

( 2 ) INFORMATION FOR SEQ ID NO:37:

( i ) SEQUENCE CHARACTERISTICS:
      ( A ) LENGTH: 6
      ( B ) TYPE: AMINO ACID
      ( C ) STRANDEDNESS: Not Relevant
      ( D ) TOPOLOGY: CIRCULAR ( i i ) MOLECULE TYPE:
      ( A ) DESCRIPTION: PEPTIDE ( x i ) SEQUENCE DESCRIPTION: SEQ ID NO: 37:

Xaa  Thr  Xaa  Xaa  Xaa  Xaa
      1                  5

( 2 ) INFORMATION FOR SEQ ID NO:38:

( i ) SEQUENCE CHARACTERISTICS:
      ( A ) LENGTH: 6
      ( B ) TYPE: AMINO ACID
      ( C ) STRANDEDNESS: Not Relevant
      ( D ) TOPOLOGY: CIRCULAR ( i i ) MOLECULE TYPE:
      ( A ) DESCRIPTION: PEPTIDE ( x i ) SEQUENCE DESCRIPTION: SEQ ID NO: 38:

```
Xaa Thr Xaa Xaa Xaa Xaa
 1               5
```

( 2 ) INFORMATION FOR SEQ ID NO:39:

( i ) SEQUENCE CHARACTERISTICS:
   ( A ) LENGTH: 6
   ( B ) TYPE: AMINO ACID
   ( C ) STRANDEDNESS: Not Relevant
   ( D ) TOPOLOGY: CIRCULAR ( i i ) MOLECULE TYPE:
   ( A ) DESCRIPTION: PEPTIDE ( x i ) SEQUENCE DESCRIPTION: SEQ ID NO: 39:

```
Xaa Thr Xaa Xaa Xaa Xaa
 1               5
```

( 2 ) INFORMATION FOR SEQ ID NO:40:

( i ) SEQUENCE CHARACTERISTICS:
   ( A ) LENGTH: 6
   ( B ) TYPE: AMINO ACID
   ( C ) STRANDEDNESS: Not Relevant
   ( D ) TOPOLOGY: CIRCULAR ( i i ) MOLECULE TYPE:
   ( A ) DESCRIPTION: PEPTIDE ( x i ) SEQUENCE DESCRIPTION: SEQ ID NO: 40:

```
Xaa Ser Xaa Xaa Xaa Xaa
 1               5
```

( 2 ) INFORMATION FOR SEQ ID NO:41:

( i ) SEQUENCE CHARACTERISTICS:
   ( A ) LENGTH: 6
   ( B ) TYPE: AMINO ACID
   ( C ) STRANDEDNESS: Not Relevant
   ( D ) TOPOLOGY: CIRCULAR ( i i ) MOLECULE TYPE:
   ( A ) DESCRIPTION: PEPTIDE ( x i ) SEQUENCE DESCRIPTION: SEQ ID NO: 41:

```
Xaa Thr Xaa Xaa Xaa Xaa
 1               5
```

( 2 ) INFORMATION FOR SEQ ID NO:42:

( i ) SEQUENCE CHARACTERISTICS:
   ( A ) LENGTH: 6
   ( B ) TYPE: AMINO ACID
   ( C ) STRANDEDNESS: Not Relevant
   ( D ) TOPOLOGY: CIRCULAR ( i i ) MOLECULE TYPE:
   ( A ) DESCRIPTION: PEPTIDE ( x i ) SEQUENCE DESCRIPTION: SEQ ID NO: 42:

```
Xaa Thr Xaa Xaa Xaa Xaa
 1               5
```

( 2 ) INFORMATION FOR SEQ ID NO:43:

( i ) SEQUENCE CHARACTERISTICS:
   ( A ) LENGTH: 6
   ( B ) TYPE: AMINO ACID (C) STRANDEDNESS: Not Relevant
(D) TOPOLOGY: CIRCULAR (i i) MOLECULE TYPE:
(A) DESCRIPTION: PEPTIDE (x i) SEQUENCE DESCRIPTION: SEQ ID NO: 43:

```
Xaa  Thr  Xaa  Xaa  Xaa  Xaa
 1                 5
```

(2) INFORMATION FOR SEQ ID NO:44:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (i i) MOLECULE TYPE:
(A) DESCRIPTION: PEPTIDE (x i) SEQUENCE DESCRIPTION: SEQ ID NO: 44:

```
Xaa  Thr  Xaa  Xaa  Xaa  Xaa
 1                 5
```

(2) INFORMATION FOR SEQ ID NO:45:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (i i) MOLECULE TYPE:
(A) DESCRIPTION: PEPTIDE (x i) SEQUENCE DESCRIPTION: SEQ ID NO: 45:

```
Xaa  Thr  Xaa  Xaa  Xaa  Xaa
 1                 5
```

(2) INFORMATION FOR SEQ ID NO:46:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (i i) MOLECULE TYPE:
(A) DESCRIPTION: PEPTIDE (x i) SEQUENCE DESCRIPTION: SEQ ID NO: 46:

```
Xaa  Thr  Xaa  Xaa  Xaa  Xaa
 1                 5
```

(2) INFORMATION FOR SEQ ID NO:47:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (i i) MOLECULE TYPE:
(A) DESCRIPTION: PEPTIDE (x i) SEQUENCE DESCRIPTION: SEQ ID NO: 47:

```
Xaa  Thr  Xaa  Xaa  Xaa  Xaa
 1                 5
```

( 2 ) INFORMATION FOR SEQ ID NO:48:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 48:

Xaa  Thr  Xaa  Xaa  Xaa  Xaa
        1                           5

( 2 ) INFORMATION FOR SEQ ID NO:49:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 49:

Xaa  Thr  Xaa  Xaa  Xaa  Xaa
        1                           5

( 2 ) INFORMATION FOR SEQ ID NO:50:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 50:

Xaa  Thr  Xaa  Xaa  Xaa  Xaa
        1                           5

( 2 ) INFORMATION FOR SEQ ID NO:51:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 51:

Xaa  Thr  Xaa  Xaa  Xaa  Xaa
        1                           5

( 2 ) INFORMATION FOR SEQ ID NO:52:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 52:

```
            Xaa  Thr  Xaa  Xaa  Xaa  Xaa
             1                5
```

( 2 ) INFORMATION FOR SEQ ID NO:53:

( i ) SEQUENCE CHARACTERISTICS:
     ( A ) LENGTH: 6
     ( B ) TYPE: AMINO ACID
     ( C ) STRANDEDNESS: Not Relevant
     ( D ) TOPOLOGY: CIRCULAR ( i i ) MOLECULE TYPE:
     ( A ) DESCRIPTION: PEPTIDE ( x i ) SEQUENCE DESCRIPTION: SEQ ID NO: 53:

```
            Xaa  Thr  Xaa  Xaa  Xaa  Xaa
             1                5
```

( 2 ) INFORMATION FOR SEQ ID NO:54:

( i ) SEQUENCE CHARACTERISTICS:
     ( A ) LENGTH: 6
     ( B ) TYPE: AMINO ACID
     ( C ) STRANDEDNESS: Not Relevant
     ( D ) TOPOLOGY: CIRCULAR ( i i ) MOLECULE TYPE:
     ( A ) DESCRIPTION: PEPTIDE ( x i ) SEQUENCE DESCRIPTION: SEQ ID NO: 54:

```
            Xaa  Thr  Xaa  Xaa  Xaa  Xaa
             1                5
```

( 2 ) INFORMATION FOR SEQ ID NO:55:

( i ) SEQUENCE CHARACTERISTICS:
     ( A ) LENGTH: 6
     ( B ) TYPE: AMINO ACID
     ( C ) STRANDEDNESS: Not Relevant
     ( D ) TOPOLOGY: CIRCULAR ( i i ) MOLECULE TYPE:
     ( A ) DESCRIPTION: PEPTIDE ( x i ) SEQUENCE DESCRIPTION: SEQ ID NO: 55:

```
            Xaa  Thr  Xaa  Xaa  Xaa  Xaa
             1                5
```

( 2 ) INFORMATION FOR SEQ ID NO:56:

( i ) SEQUENCE CHARACTERISTICS:
     ( A ) LENGTH: 6
     ( B ) TYPE: AMINO ACID
     ( C ) STRANDEDNESS: Not Relevant
     ( D ) TOPOLOGY: CIRCULAR ( i i ) MOLECULE TYPE:
     ( A ) DESCRIPTION: PEPTIDE ( x i ) SEQUENCE DESCRIPTION: SEQ ID NO: 56:

```
            Xaa  Thr  Xaa  Xaa  Xaa  Xaa
             1                5
```

( 2 ) INFORMATION FOR SEQ ID NO:57:

( i ) SEQUENCE CHARACTERISTICS:
     ( A ) LENGTH: 6
     ( B ) TYPE: AMINO ACID
     ( C ) STRANDEDNESS: Not Relevant
     ( D ) TOPOLOGY: CIRCULAR ( i i ) MOLECULE TYPE:

( A ) DESCRIPTION: PEPTIDE ( x i ) SEQUENCE DESCRIPTION: SEQ ID NO: 57:

```
Xaa  Thr  Xaa  Xaa  Xaa  Xaa
 1               5
```

( 2 ) INFORMATION FOR SEQ ID NO:58:

( i ) SEQUENCE CHARACTERISTICS:

( A ) LENGTH: 6
   ( B ) TYPE: AMINO ACID
   ( C ) STRANDEDNESS: Not Relevant
   ( D ) TOPOLOGY: CIRCULAR ( i i ) MOLECULE TYPE:

( A ) DESCRIPTION: PEPTIDE ( x i ) SEQUENCE DESCRIPTION: SEQ ID NO: 58:

```
Xaa  Thr  Xaa  Xaa  Xaa  Xaa
 1               5
```

( 2 ) INFORMATION FOR SEQ ID NO:59:

( i ) SEQUENCE CHARACTERISTICS:

( A ) LENGTH: 6
   ( B ) TYPE: AMINO ACID
   ( C ) STRANDEDNESS: Not Relevant
   ( D ) TOPOLOGY: CIRCULAR ( i i ) MOLECULE TYPE:

( A ) DESCRIPTION: PEPTIDE ( x i ) SEQUENCE DESCRIPTION: SEQ ID NO: 59:

```
Xaa  Thr  Xaa  Xaa  Xaa  Xaa
 1               5
```

( 2 ) INFORMATION FOR SEQ ID NO:60:

( i ) SEQUENCE CHARACTERISTICS:

( A ) LENGTH: 6
   ( B ) TYPE: AMINO ACID
   ( C ) STRANDEDNESS: Not Relevant
   ( D ) TOPOLOGY: CIRCULAR ( i i ) MOLECULE TYPE:

( A ) DESCRIPTION: PEPTIDE ( x i ) SEQUENCE DESCRIPTION: SEQ ID NO: 60:

```
Xaa  Thr  Xaa  Xaa  Xaa  Xaa
 1               5
```